United States Patent
Sundararaman et al.

(10) Patent No.: US 10,810,223 B2
(45) Date of Patent: Oct. 20, 2020

(54) DATA PLATFORM FOR AUTOMATED DATA EXTRACTION, TRANSFORMATION, AND/OR LOADING

(71) Applicant: Accenture Global Solutions Limited, Dublin (IE)

(72) Inventors: Arun Sundararaman, Chennai (IN); Udayakumar Ramamoorthy, Tamilnadu (IN); Sureshkumar Pargunarajan, Tamilnadu (IN); Sangeetha Appusamy, Tamilnadu (IN)

(73) Assignee: Accenture Global Solutions Limited, Dublin (IE)

( * ) Notice: Subject to any disclaimer, the term of this patent is extended or adjusted under 35 U.S.C. 154(b) by 286 days.

(21) Appl. No.: 16/008,602

(22) Filed: Jun. 14, 2018

(65) Prior Publication Data

US 2019/0384849 A1 Dec. 19, 2019

(51) Int. Cl.
*G16H 30/20* (2018.01)
*G06N 20/00* (2019.01)
*G06F 16/25* (2019.01)
*G06F 9/455* (2018.01)

(52) U.S. Cl.
CPC ........ *G06F 16/254* (2019.01); *G06F 9/45533* (2013.01); *G06F 16/258* (2019.01); *G06N 20/00* (2019.01); *G16H 30/20* (2018.01); *G06F 2009/45595* (2013.01)

(58) Field of Classification Search
CPC .. G06F 16/254; G06F 16/258; G06F 9/45533; G06F 2009/45595; G16H 30/20; G06N 20/00
See application file for complete search history.

(56) References Cited

U.S. PATENT DOCUMENTS

| 10,628,553 | B1* | 4/2020 | Murrish | G06F 19/32 |
| 2007/0260492 | A1* | 11/2007 | Feied | G16H 10/60 |
| | | | | 705/3 |
| 2009/0138803 | A1* | 5/2009 | Laxminarayan | G06Q 20/14 |
| | | | | 715/742 |

(Continued)

OTHER PUBLICATIONS

Hutchison et al., Electronic Data Interchange for Health Care, IEEE, Jul. 1996, all pages. (Year: 1996).*

*Primary Examiner* — Jay A Morrison
*Assistant Examiner* — Antonio J Caiado
(74) *Attorney, Agent, or Firm* — Harrity & Harrity, LLP

(57) ABSTRACT

A data platform may receive data files from an electronic data interchange (EDI). The data files may be received in multiple different data formats. The data platform may convert the data files to a common data format, extract data elements from the data files converted to the common data format, and assign the data elements extracted from the data files to file identifiers. The data platform may assign the data elements extracted from the data files to attribute identifiers that identify types of data represented by the data elements, aggregate the data elements to create a standardized data set, and map the data elements in the standardized data set to functions. The data platform may generate values based on mapping the data elements to the functions, determine a metric based on combining the values according to a metric definition, and post the metric to the EDI for consumption.

20 Claims, 11 Drawing Sheets

(56) References Cited

U.S. PATENT DOCUMENTS

| | | | |
|---|---|---|---|
| 2010/0274580 A1* | 10/2010 | Crownover | G06Q 10/04 |
| | | | 705/2 |
| 2011/0119088 A1* | 5/2011 | Gunn | G06F 19/00 |
| | | | 705/3 |
| 2011/0173346 A1 | 7/2011 | Neben | |
| 2013/0332194 A1* | 12/2013 | D'Auria | G16H 10/60 |
| | | | 705/3 |
| 2014/0046697 A1 | 2/2014 | Rogers et al. | |
| 2015/0317337 A1* | 11/2015 | Edgar | G06F 19/328 |
| | | | 707/751 |
| 2016/0019357 A1* | 1/2016 | Marzula | G06F 19/328 |
| | | | 705/2 |
| 2016/0063191 A1 | 3/2016 | Vesto et al. | |
| 2016/0063209 A1 | 3/2016 | Malaviya | |
| 2020/0013124 A1* | 1/2020 | Obee | G06N 5/022 |

\* cited by examiner

DATA PLATFORM FOR AUTOMATED DATA EXTRACTION, TRANSFORMATION, AND/OR LOADING

BACKGROUND

As more and more industries become digitized, it is not uncommon for different kinds of information to be exchanged electronically. The healthcare industry is one in which an Electronic Data Interchange (EDI) plays a central role in facilitating the electronic communication and exchange of healthcare related data, including, for example, data pertaining to health insurance claims, health insurance enrollment, eligibility data, claims settlement, medical records, and/or the like. The Health insurance Portability and Accountability Act (HIPAA) has led to standardized claims administration and automation in the healthcare industry by employing EDI messages to exchange data.

SUMMARY

According to some possible implementations, a method may include receiving, by a computing resource of a cloud computing environment, a plurality of data files from a healthcare electronic data interchange (EDI). The plurality of data files may be received in a plurality of different data formats, and the plurality of data files may include data elements associated with healthcare data. The method may include converting, by a computing resource of the cloud computing environment, the plurality of data files received in the plurality of different data formats to a common data format. The method may include extracting, by a computing resource of the cloud computing environment, data elements from the plurality of data files converted to the common data format. The method may include assigning, by a computing resource of the cloud computing environment, the data elements extracted from the plurality of data files to file identifiers that identify from which of the plurality of data files the data elements were extracted. The method may include assigning, by a computing resource of the cloud computing environment, the data elements extracted from the plurality of data files to attribute identifiers that identify types of healthcare data represented by the data elements. The method may include aggregating, by a computing resource of the cloud computing environment, the data elements based on the file identifiers and the attribute identifiers to create a standardized data set. The method may include mapping, by a computing resource of the cloud computing environment, the data elements in the standardized data set to a plurality of functions contained in at least one function library based on a mapping between the attribute identifiers and the plurality of functions. The method may include generating, by a computing resource of the cloud computing environment, a plurality of values based on mapping the data elements to the plurality of functions. The method may include determining, by a computing resource of the cloud computing environment, a healthcare metric based on combining the plurality of values according to a healthcare metric definition. The method may include posting, by a computing resource of the cloud computing environment, the healthcare metric to the healthcare EDI for consumption by healthcare data clients.

According to some possible implementations, a device may include one or more memories, and one or more processors, communicatively coupled to the one or more memories, to receive a plurality of data files. The plurality of data files may be received in a plurality of different data formats, and the plurality of data files may include data elements associated with healthcare data. The one or more processors may convert the plurality of data files received in the plurality of different data formats to a common data format, extract data elements from the plurality of data files converted to the common data format, assign the data elements extracted from the plurality of data files to file identifiers that identify from which of the plurality of data files the data elements were extracted, and assign the data elements extracted from the plurality of data files to attribute identifiers that identify types of healthcare data represented by the data elements. The one or more processors may aggregate the data elements based on the file identifiers and the attribute identifiers to create a standardized data set, examine the standardized data set to identify the attribute identifiers present in the standardized data set, and determine, using a data model, a list of healthcare metrics that are derivable from the standardized data set based on the attribute identifiers present in the standardized data set. The one or more processors may map the data elements in the standardized data set to a plurality of functions based on a mapping between the attribute identifiers and the plurality of functions. The plurality of functions may be configured to generate a healthcare metric included in the list of healthcare metrics. The one or more processors may generate a plurality of values based on processing the data elements using the plurality of functions, derive the healthcare metric based on combining the plurality of values according to a healthcare metric definition, and post the healthcare metric to a healthcare electronic data interchange (EDI) for consumption by healthcare data client.

According to some possible implementations, a non-transitory computer-readable medium may store one or more instructions that, when executed by one or more processors, cause the one or more processors to receive a plurality of data files. The plurality of data files may be received in a plurality of different data formats. The plurality of data files may include data elements. The one or more instructions, when executed by the one or more processors, may cause the one or more processors to convert the plurality of data files received in the plurality of different data formats to a common data format, and extract data elements from the plurality of data files converted to the common data format. The one or more instructions, when executed by the one or more processors, may cause the one or more processors to assign the data elements extracted from the plurality of data files to file identifiers that identify from which of the plurality of data files the data elements were extracted, and assign the data elements extracted from the plurality of data files to attribute identifiers that identify types of data represented by the data elements. The one or more instructions, when executed by the one or more processors, may cause the one or more processors to examine a data file of the plurality of data files to identify a combination of data elements present in the data file, and determine, using a first machine learning model, a first score for a data element in the data file based on the combination of data elements present in the data file. The first score may predict a type of data represented by the data element based on the combination of data elements present in the data file. The one or more instructions, when executed by the one or more processors, may cause the one or more processors to assign the data element to an attribute identifier based on the first score, aggregate the data elements based on the file identifiers and the attribute identifiers to create a standardized data set, and map the data elements in the standardized data set to a plurality of functions contained in at least one function library based on a mapping between the attribute identifiers and the plurality of functions. The one or more instructions, when executed by the one or more processors, may cause the one or more processors to generate a plurality of values based on mapping the data elements to the plurality of functions, derive a metric based on combining the plurality of values according to a metric definition, and post the metric to an electronic data interchange (EDI) for consumption by data clients.

DETAILED DESCRIPTION

Figure 1A:
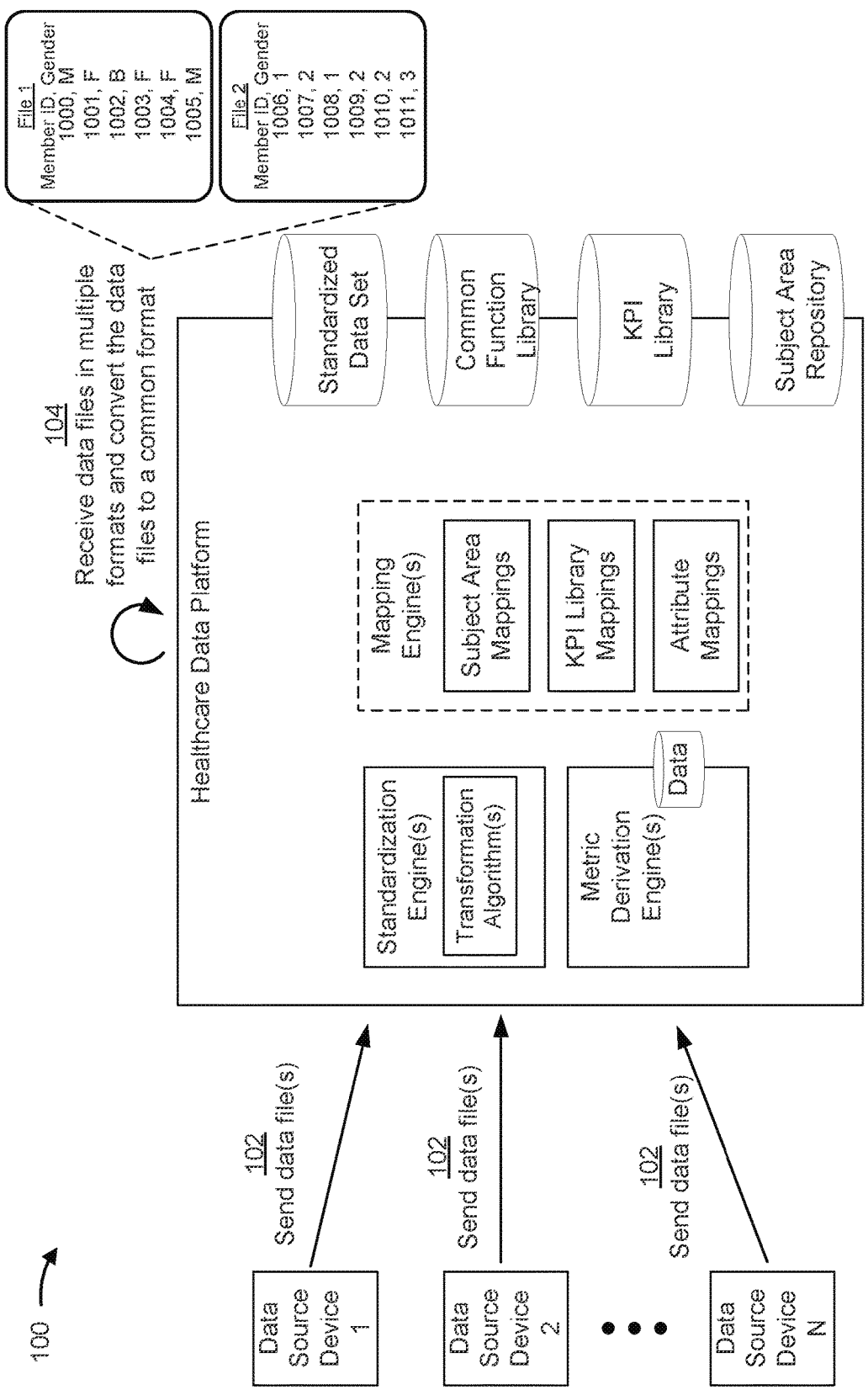
FIGS. 1A-1E are diagrams of an example implementation described herein.

The following detailed description of example implementations refers to the accompanying drawings. The same reference numbers in different drawings may identify the same or similar elements.

The healthcare industry is one of many industries that produces an enormous amount of data, including healthcare related data in the form of medical records, hospital records, primary care physician records, billing records, health insurance records (e.g., eligibility data, enrollment data, claims records, claims information, paid amounts, declined amounts, etc.), and/or the like. The data may be transmitted, received, exchanged, and/or otherwise communicated by various entities in various formats using an electronic data interchange (EDI). The EDI facilitates the secure, electronic exchange of data in a variety of standardized formats for use by various healthcare clients (e.g., healthcare professionals, healthcare institutions (e.g., hospitals, primary care physicians, etc.), insurance clients, and/or the like). The various healthcare clients may employ one or more data analytics tools to access and manipulate the enormous amount of data available from the EDI, for example, to assess trends, measure key performance indicators (KPIs), calculate metrics for driving decisions to deliver better medical care, calculate metrics for driving decisions to reduce waste, and/or the like.

The various entities that send, receive, exchange, or otherwise communicate data by way of the EDI may encode the data using specific industry notations. In some cases, different healthcare providers (e.g., hospitals, primary care providers, etc.) may encode the same data differently. As an example, one healthcare provider may indicate a patient's gender using alphabetic characters "M", "F", and/or the like, while another healthcare provider may indicate a patient's gender using numeric characters "1", "2", and/or the like. Decoding the data communicated by the EDI may prove to be a daunting and difficult task. Some data analytics tools may employ exhaustive computer coding efforts and/or a large number of data processing resources to decode the enormous amount of data communicated by the EDI. In many instances, some data analytics tools include exorbitant licensing fees associated with accessing or obtaining proprietary software to decode the data.

Similarly, the various entities that send, receive, exchange, or otherwise communicate data by way of the EDI may encode the data in one of many different EDI formats (e.g., HL7, NCPDP, JSON, and/or the like). Some data analytics tools may rely on predefined tables and data structures that transform the data based on a rigid set of rules, typically rules that only transform the data received in a single EDI format. Such rigidity leads to limited data abstraction and restricted analyses. Additionally, collaboration between different healthcare clients may be inhibited or further complicated, given that the different healthcare clients may utilize different technological infrastructures.

Some implementations described herein provide a flexible, intelligent computing platform, such as a healthcare data platform, for analyzing large amounts of data communicated by a healthcare EDI. In some implementations, the healthcare data platform may be configured to standardize the data communicated by the healthcare EDI, for example, by decoding and/or decoupling the data from specific industry notations and/or EDI formats. In this way, the healthcare platform may provide a more comprehensive and thorough data analytics platform. The healthcare data platform may utilize standardized data sets and intelligent mappings to perform more efficient, uniform, consistent, and/or automated data transformations using the data communicated by the healthcare EDI. For example, the data received from the healthcare EDI may be converted to a common format, assigned various attribute identifiers, and/or logically grouped for use in deriving various healthcare metrics. The healthcare metrics may be transmitted or posted to the EDI for consumption by various clients. The clients may additionally be caused to perform one or more actions based on the metrics. As an example, a client may perform actions including paying a claim, denying a claim, enrolling an individual in an insurance policy or plan, assigning a member to a healthcare provider, and/or the like, based on the metrics derived by the healthcare data platform.

In some implementations, a plurality of functions or logic may be stored in one or more collections or libraries available to the healthcare data platform. Such functions may facilitate the provision of common data transformations and/or metric computations using the common data transformations. For example, the logic for computing a common data transformation (e.g., primary care physician attribution, provider matching, KPIs, and/or the like) may be reused, rendering the computation of such functions and metrics more efficient, automated, and/or consistent. In this way, compute coding efforts and computing resources that would otherwise be needed to perform multiple iterations of the common data transformation of data are greatly reduced or obviated.

Additionally, or alternatively, the healthcare data platform may use machine learning and/or artificial intelligence to make intelligent predictions, mappings, and/or groupings of data to improve the overall process of performing data transformations and analyses. For example, the healthcare data platform may train data models on historical data that may be used to predict and/or classify newly obtained data from the healthcare EDI, by assigning the data to specific healthcare subject areas, deriving lists of possible metrics based on data elements present in the newly obtained data, and/or the like. In this way, the analysis of data obtained from the healthcare EDI may be more automated, efficient, and consistent. Further, the amount of computing resources needed to decode the data received from the healthcare EDI may be obviated or reduced.

The healthcare data platform may improve an efficiency of analyzing healthcare data associated with processes and/or operations being performed by various data sources or clients. In addition, the intelligent predictions and/or mappings employed by the healthcare data platform may conserve processing resources that would otherwise be consumed by efforts to decode the data obtained from the EDI, perform rigid transformations of the data, and/or perform inefficient operations.

While implementations, described herein, will be described in the context of healthcare data, one or more of these implementations may be applied outside of this context. For example, one or more of these implementations may be applied in other contexts, such as in a financial data context, a government record context, a military record context, a census data context, and/or the like.

FIGS. 1A-1E are diagrams of an example implementation 100 described herein. As shown in FIGS. 1A-1E, example implementation 100 may include a healthcare data platform. The healthcare data platform may include standardization engine(s), which may include transformation algorithm(s) data transformation algorithm(s) and reusable methods and functions for carrying out data transformations on healthcare data sets e.g., deriving member spans from multiple coverages, member matching, provider matching, healthcare claims submissions to Centers for Medicare & Medicaid Services (CMS), etc. The healthcare data platform may further include metric derivation engine(s), which may generate various metrics. The healthcare data platform may further include mapping engine(s), which may include subject area mappings, KPI library mappings, and/or attribute mappings. The healthcare data platform may generate a standardized data set and, in some implementations, employ intelligent mappings for mapping data elements in the standardized data set to functions in a common function library, functions in a KPI library, and/or a subject area repository.

As shown in FIG. 1A, and by reference number 102, a plurality of data source devices may send a plurality of data files. The data source devices may include computers or servers associated with one or more healthcare entities (e.g., healthcare providers, offices, hospitals, pharmacies, insurance companies, etc.). In some implementations, the data source devices may transmit the data files using a healthcare EDI. The data files may include or contain healthcare data or healthcare related data, including, for example, health insurance data, health insurance claims data, patient or member data, enrollment data, medical records, pharmaceutical records, payment records, billing records, and/or the like. In some implementations, the healthcare data may be encoded as data elements (e.g., metadata) in the data files. The healthcare data platform can receive and analyze millions, billions, trillions, etc., of data records and/or data elements, the volume of which cannot be processed objectively by human actors.

In some implementations, the data elements contained in the data files may indicate information relating to a patient (e.g., a patient gender, name, member identifier, age, date of birth, etc.), information relating to a medical claim (e.g., date(s) of service, a healthcare provider identifier, a billed amount, a paid amount, a denied amount, etc.), information relating to a medical condition or treatment (e.g., medical condition(s) identified, medical service(s) performed or received, lab work performed, pharmaceuticals prescribed, etc.), information relating to a healthcare provider (e.g., a hospital identifier, a physician or doctor identifier, etc.), and/or the like.

In some implementations, the plurality of data files sent by the plurality of data source devices may be transmitted in a plurality of different data formats. Example data formats include, without limitation, HL7 messaging formats, DICOM messaging formats, XML messaging formats, JSON messaging formats, NCPDP messaging formats, and/or the like.

As further shown in FIG. 1A, and by reference number 104, the healthcare data platform may receive the data files from the plurality of data source devices. In some implementations, the healthcare data platform may receive the data files from the healthcare EDI. For example, the healthcare data platform may subscribe to receive data from the healthcare EDI. In some implementations, the data files may be received in one or more different ways. For example, the data files may be streamed, obtained using API calls, pushed, fetched, and/or received in batches from the healthcare EDI.

As indicated above, the data files may be sent by the data source devices and received by the healthcare data platform in multiple different data formats. In some implementations, the healthcare data platform may convert the data files received in the multiple different data formats to a common format. As an example, the data files received in HL7, DICOM, XML, JSON, and/or NCPDP messaging formats may be converted to Comma Separated Value (CSV) files using code or logic to perform the CSV conversion. Example files are shown in FIG. 1A.

Continuing with respect to reference number 104, as shown, the healthcare data platform may convert a first data file received from a first data source to a first CSV file having the file identifier "File 1", and the healthcare data platform may convert a second data file received from a second data source to a second CSV file having the file identifier "File 2". In some implementations, the healthcare data platform may convert the incoming or received data files to the same CSV format. For example, assume that the data elements in the first data file correspond to a plurality of member identifiers and genders associated with the member identifiers. Here, assume that the first data source transmitting the first data file uses the alphabetic characters "M", "F", and "B" to indicate the member's gender. Further assume that the data elements in the second data file also correspond to a plurality of member identifiers and genders associated with the member identifiers. However, in contrast to the notations employed by the first data source, assume that the second data source uses numerals "1", "2", and "3" to indicate the member's gender. As described herein, the healthcare data platform may apply a data standardization reference rules library to determine that "M" and "1" both identify the same attribute (e.g., male).

In some implementations, the healthcare data platform may validate the decimal and integer fields associated with the data elements in the data files during or after conversion to the common format. For example, for data elements associated with a date, the healthcare data platform may convert multiple date formats (e.g., 01/01/2018, 01-01-2018, 01/11/18, etc.) to a common format. In some implementations, the decimal and integer fields may be validated to ensure that the data elements are consistent with the common format.

Figure 1B:
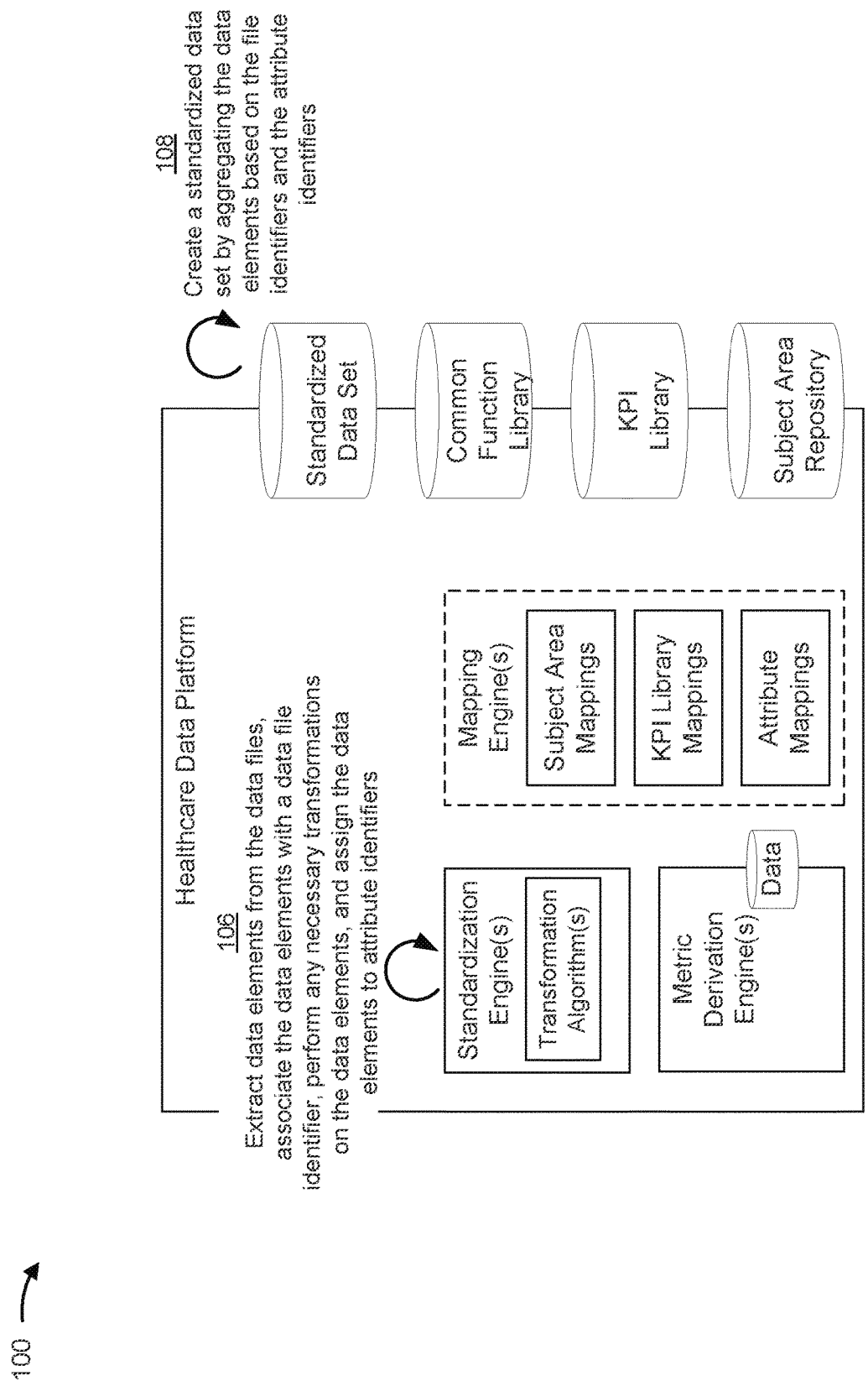

As shown in FIG. 1B, and by reference number 106, the healthcare data platform may extract the data elements from the data files converted to the common format, associate the data elements with file identifiers (e.g., "File 1", "File 2", etc.), perform any necessary transformations on the data elements, and assign the data elements to attribute identifiers. The attribute identifiers may be predetermined, standardized, and/or predefined identifiers that label, classify, or otherwise identify the type of data (e.g., member data (e.g., health insurance member identifier, age, date of birth, etc.), claim data (e.g., service date, claim amount, balance due, etc.), healthcare provider data (e.g., healthcare provider identifier, a hospital, healthcare provider address, etc.), pharmacy data (e.g., a prescription identifier, a medication identifier, etc.), and/or the like) that is represented by the respective data element. In this way, the data received from the healthcare EDI may be standardized and homogenized, for example, using one or more standardization engines of the healthcare data platform.

Initially, in some implementations, the healthcare data platform may extract the data elements from the data files and associate the extracted data elements with file identifiers. In this case, the file identifiers may identify a data file from which the data elements are extracted. For example, the member identifier and gender data elements may be extracted from the first CSV file, as described above with respect to FIG. 1A, and may be associated with the file identifier "File 1". Similarly, the member identifier and gender data elements may be extracted from the second CSV fife, as described above with respect to FIG. 1A, and may be associated with the file identifier "File 2". The healthcare data platform may perform the data file conversion, data element extraction, and data element assignment for thousands, millions, billions, etc., of data files over any given time period (e.g., an hour, a day, a week, etc.).

In some implementations, the healthcare data platform may perform preliminary cleansing of the data elements before assigning the data elements to attribute identifiers to ensure elimination of redundant data and ensure that valid data is processed by the healthcare data platform. The invalid data may be reconciled by error handling routines. In this way, the healthcare data platform may perform common data validation of data elements in a data set to eliminate redundancy without compromising validity. For example, the transformation algorithms and/or functions obtained from the common function library may be used to deduplicate redundant data elements in the data files and/or match claims to adjudicated amounts for use in determining various metrics as described further below.

In some implementations, the healthcare data platform may assign, label, or classify the extracted data elements in the data files based on predetermined or predefined attribute identifiers. In this way, any specific notations (e.g., M, F, 1, 2, etc.) may be removed, obviated, standardized, and/or homogenized. In some implementations, the healthcare data platform may access data structures or mappings for assigning the data elements to the attribute identifiers. For example, the healthcare data platform may employ one or more mapping engines based on a healthcare subject area and one or more attribute data structures containing mappings (e.g., tables, catalogs, databases, etc.) to assign or map the data elements and the predefined attribute identifiers. Continuing with the example in FIG. 1A, the "M" in File 1 and the "1" in File 2 may each be assigned to the attribute identifier "Male". In this way, the data files are assigned to standardized attribute identifiers. Similarly, the "F" in File 1 and the "2" in File 2 may each be assigned to the common attribute identifier "Female". Similarly, the "B" in File 1 and the "3" in File 2 may each be assigned to the common attribute identifier "Non-Identifying". In this way, occurrences of different notations may be obviated from a data set, which conserves computing resources that would otherwise be needed to decode the data elements upon using the data elements to calculate metrics or KPIs.

In some implementations, the data structures or mappings used to assign the data elements to the attribute identifiers may be compiled based on historical data and a machine learning model. For example, the machine learning model may use, as input, historical data based on knowledge of the data element notations being implemented by specific data sources to determine assignments for newly received data elements in data files received from the same data sources. For example, the healthcare data platform may receive a file from the first data source, which the healthcare data platform recognizes as Hospital Z. The healthcare data platform may determine, based on examining historical data input to a client mapping rules engine, that Hospital Z encodes gender in the form of "1" for males, "2" for females, and "3" for non-identifying individuals. Based on this historical data, the healthcare data platform may determine that File 2 is from Hospital Z and automatically assign the data element "1" to the attribute identifier "Male" when assigning the data elements to attribute identifiers for File 2. In this way, for example, and based on this assignment scheme, computing resources that would otherwise be needed to assign the data elements to attribute identifiers may be conserved.

In some implementations, the healthcare data platform may be configured to assign the data elements to attribute identifiers based on a data model that classifies the data file according to a pattern or combination of data elements present in the data file. For example, the healthcare data platform may perform a high-level scan or assessment of a data file, upon re-formatting the data file, to initially determine what kind of information may be present in the data file. As a specific example, the healthcare data platform may scan File 2 and determine, based on the presence of the member identifiers and gender information, that File 2 is a data file for membership enrollment. Assuming that additional data elements were present in File 2, the healthcare data platform may determine which attribute identifiers to assign to the additional data elements based on determining which additional data elements, if any, are commonly present in data files for membership enrollment. For example, File 2 may include unidentified numeric values (e.g., ranging between 0-100) associated with each member identifier and gender, the healthcare data platform may determine, using the data model, to assign the unidentified numeric values to the attribute identifier "Age" based on knowledge and/or prediction that membership enrollment files typically include member identifiers, gender, and ages.

Accordingly, in some implementations, the healthcare data platform may examine a data file, of the plurality of data files, to identify a pattern or combination of data elements present in the data file. The healthcare data platform may determine, using a machine learning model, a score (e.g., a map score) for a data element in the data file based on the combination of data elements present in the data file. The score may predict a type of healthcare data (e.g., the member's age in the example above) represented by the data element based on the combination of data elements present in the data file. The healthcare data platform may then assign the data element to an attribute identifier based on the score. The data files may be classified as containing or identifying data pertaining to claim types, claim status, member types, product codes, facility types, insurance network types, adjudication outcomes, and/or the like. Data elements within such data files may be intelligently assigned to attribute identifiers based on the type of data the model predicts will be present within a given type of data file.

As further shown in FIG. 1B, and by reference number 108, the healthcare data platform may create or form a standardized data set by aggregating the data elements based on the data file identifiers and the predetermined attribute identifiers. The standardized data set may be devoid of industry or data source specific notations and/or specific EDI formats. In some implementations, the data associated with the attribute identifiers contained in the standardized data set may have been transformed using a function or logic, such as by using, for example, a common transformation algorithm or a common function.

In this way, computing resources associated with extracting, transforming, and/or aggregating data based on different logic (e.g., different algorithms, differently coded functions, etc.) for data elements specified in differing formats are reduced or obviated. The standardized data set may be used to derive, determine, compute, or calculate various healthcare metrics and/or KPIs. Various actions may be performed based on determining the healthcare metrics and/or KPIs as described below.

In some implementations, data clients, including healthcare data clients, may subscribe or otherwise access the standardized data set stored by the healthcare data platform to perform various data analyses. In this way, utilizing the standardized data set may improve the efficiency at which the various data analyses are performed. In some implementations, the healthcare data platform may calculate metrics that are accessed, used, and/or consumed by multiple data clients. In this way, the metrics may be consistently calculated irrespective of specific notations and/or EDI formats. Computing resources that would otherwise be needed to calculate the metrics for individual data clients based on specific notations and/or EDI formats are conserved, reduced, and/or obviated.

Figure 1C:
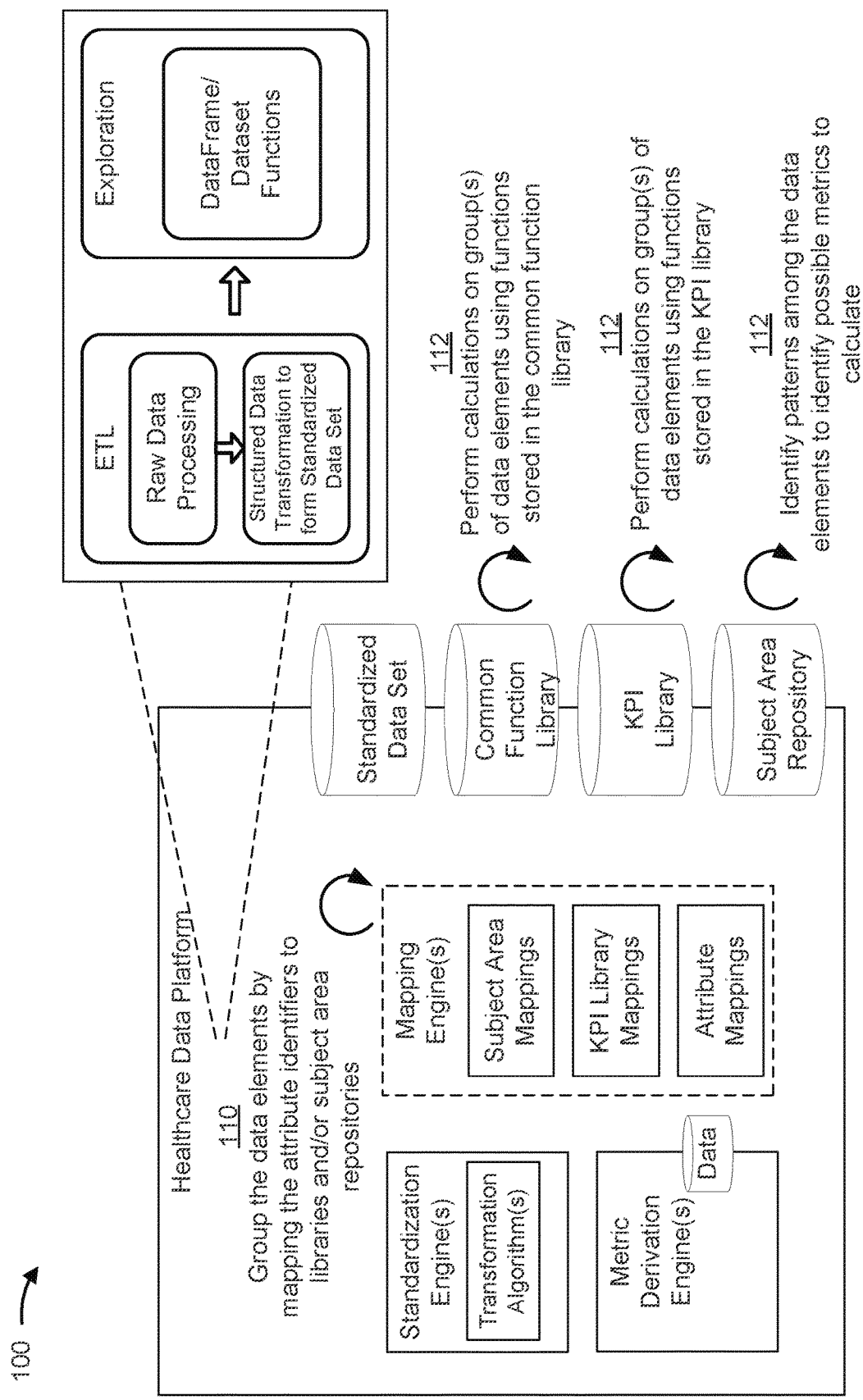

As shown in FIG. 1C, and by reference number 110, the healthcare data platform may group the data elements in the standardized data set. In some implementations, the data elements in the standardized data set may be grouped based on mapping the predetermined attribute identifiers associated with the data elements to libraries and/or subject area repositories for which the data elements may be used to perform various analyses. In some implementations, the healthcare data platform may access one or more mapping engines to map the data elements in the standardized data set to a plurality of functions contained in at least one function library, such as the common function library or the KPI library, based on a mapping between the attribute identifiers and the plurality of functions. In some implementations, the healthcare data platform may map the data elements in the standardized data set to one or more subject area repositories based on mappings between the attribute identifiers and the subject area repositories. In this way, the data sets undergo intelligent processing based on the type of data elements and automate KPI calculation depending on the subject area of the client providing extended insights to the clients.

Continuing with respect to reference number 110, as the inset in FIG. 1C shows, the raw data may be extracted, transformed, and/or loaded (i.e., ETL) into a data structure containing the standardized data set (e.g., using structured data transformations). The data in the standardized data set may be mapped to functions or repositories for further exploration and insight using the data. In some implementations, the data elements in the standardized data set may be grouped into data frames and mapped to the subject area repository, the common function library, the KPI library, and/or the like. The groupings may be based on subject area mappings, common function library mappings, and/or KPI library mappings accessed by the one or more mapping engines.

In some implementations, the healthcare data platform may intelligently group the data elements based on machine learning models or data models by which the healthcare data platform predicts the subject area repository, the common function, and/or the KPI to which the data elements correspond. For example, the healthcare data platform may examine a data file to identify a combination of data elements present in the data file. The healthcare data platform may determine, using a machine learning model or a data model, a score for the data file based on the combination of data elements present in the data file. The score may predict a subject area (e.g., a healthcare subject area) associated with the data file based on the combination of data elements present in the data file. The healthcare data platform may assign the data file and/or data elements in the data file to a subject area repository based on the score.

In this way, standardized data sets for various subject areas may be created for use in calculating various metrics specific to a given subject area. Example subject areas include, for example, a Pharmacy Claim subject area, a Provider subject area, a Medical Claim subject area, a Member subject area, and/or the like. Data files and/or data elements used to perform specific subject area operations may be assigned to and/or stored in the various subject area repositories. As an example, a PCP repository may include data files and/or data elements used to perform PCP-specific operations including PCP attribution, PCP matching, and/or the like. A health insurance claims subject area repository may include data files and/or data elements used to perform claims-specific operations or calculations, including, for example, calculations for determining late payment penalties incurred on adjusted claims, the number of claims denied during a specified period, the average claims processing or cycle time, the total number of claims received, and/or the like.

In some implementations, the data elements may be assigned to subject area repositories and/or functions based on unique keywords specific to the subject area and/or function. For example, incoming data files including the keywords "dependent" and/or "QHP" may be correlated and/or assigned to a member subject area repository and/or functions that may utilize member information contained in such data files. Similarly, data files that include keywords related to a specific payer or a specific diagnostic code may be correlated and/or assigned to a health insurance claims subject area repository and/or functions that may utilize claims information contained in such data files.

In some implementations, the healthcare data platform may intelligently map data elements in the standardized data set and/or the subject area repositories to KPIs contained in the KPI library. Various KPIs may be defined or configured in the KPI library. The KPI definitions or configurations may include mathematical formulas based on manipulating data elements that correspond to specified attribute identifiers. In some implementations, the attribute identifiers in the standardized data set and/or subject area repositories may be identified, matched to KPI definitions, and mapped to the KPI definitions in the KPI library.

As further shown in FIG. 1C, and by reference number 112, the healthcare data platform may perform various actions based on the groupings or mappings between the attribute identifiers, the libraries (e.g., common function library, KPI library, etc.), and/or the subject area repositories. For example, the healthcare data platform may perform calculations based on the data elements mapped to functions stored in the common function library. Example common functions include calculating amounts for paid claims, calculating amounts for denied claims, or calculations based on the life cycle of a claim. Additionally, or alternatively, the healthcare data platform may perform calculations based on the data elements mapped to functions stored in the KPI library. Example KPIs include average claims processing times, patient wait times, average lengths of stay, claims denial rates, average treatment charges by a provider, and/or the like.

Additionally, or alternatively, the healthcare data platform may identify patterns (e.g., utilizing a data model, a machine learning model, or other intelligence) among the data elements in the standardized data set and/or the subject area repositories to identify possible metrics that may be calculated based on the data elements present in the standardized data set and/or the subject area repositories. For example, the healthcare data platform may examine the standardized data set or subject area repository to identify the attribute identifiers present in the standardized data set or the subject area repository, may determine, using a data model, a list of healthcare metrics that are derivable from the standardized data set or the subject area repository based on the attribute identifiers present in the standardized data set or the subject area repository, and may present the list healthcare metrics that are derivable from the standardized data set or the subject area repository to one or more healthcare data clients.

In some implementations, the data model used to determine the metrics in the list of healthcare metrics that may be derivable from the standardized data set may be trained on training data that includes patterns of attribute identifiers. The healthcare data platform may identify a metric to include in the list of metrics using pattern recognition based on recognizing the patterns in the attribute identifiers, and generates a score (e.g., a KPI score) that predicts the ability to successfully determine the metric. The score may be compared to a threshold value (e.g., a confidence level), by which the healthcare data platform will include the metric in the list of metrics if the threshold is satisfied.

Figure 1D:
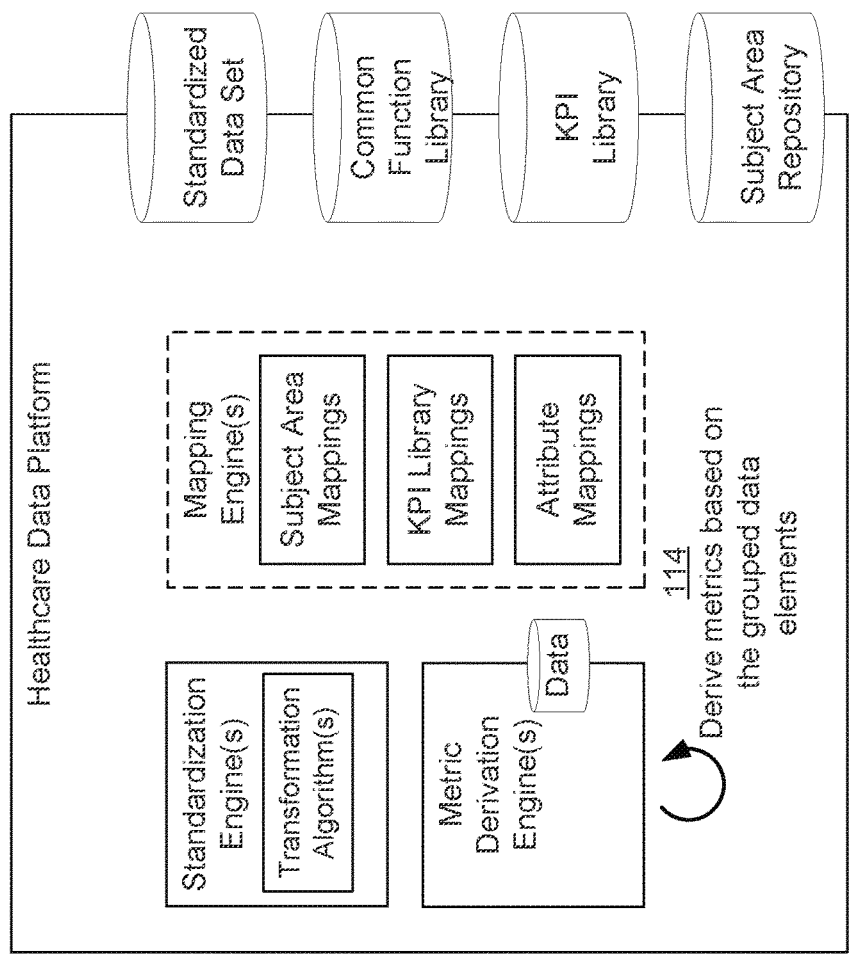

As shown in FIG. 1D, and by reference number 114, the healthcare data platform may derive, determine, generate, calculate, or compute metrics (e.g., healthcare metrics) based on the grouped data elements. For example, in some implementations, the healthcare data platform may generate a plurality of values based on mapping the data elements to the plurality of functions and may determine one or more metrics based on combining the plurality of values according to a metric definition or logic. In some implementations, the metrics may be determined by a metric derivation engine of the healthcare data platform, which accesses stored metric definitions and computes the metrics based on the stored definitions. Example metrics include per member per month (PMPM) metrics, member satisfaction metrics, community metrics (e.g., metrics relating to childhood immunizations, births, deaths, diseases, etc.), hospital metrics (e.g., average length of stay in a hospital, readmission rates, wait times, etc.) and/or the like.

Figure 1E:
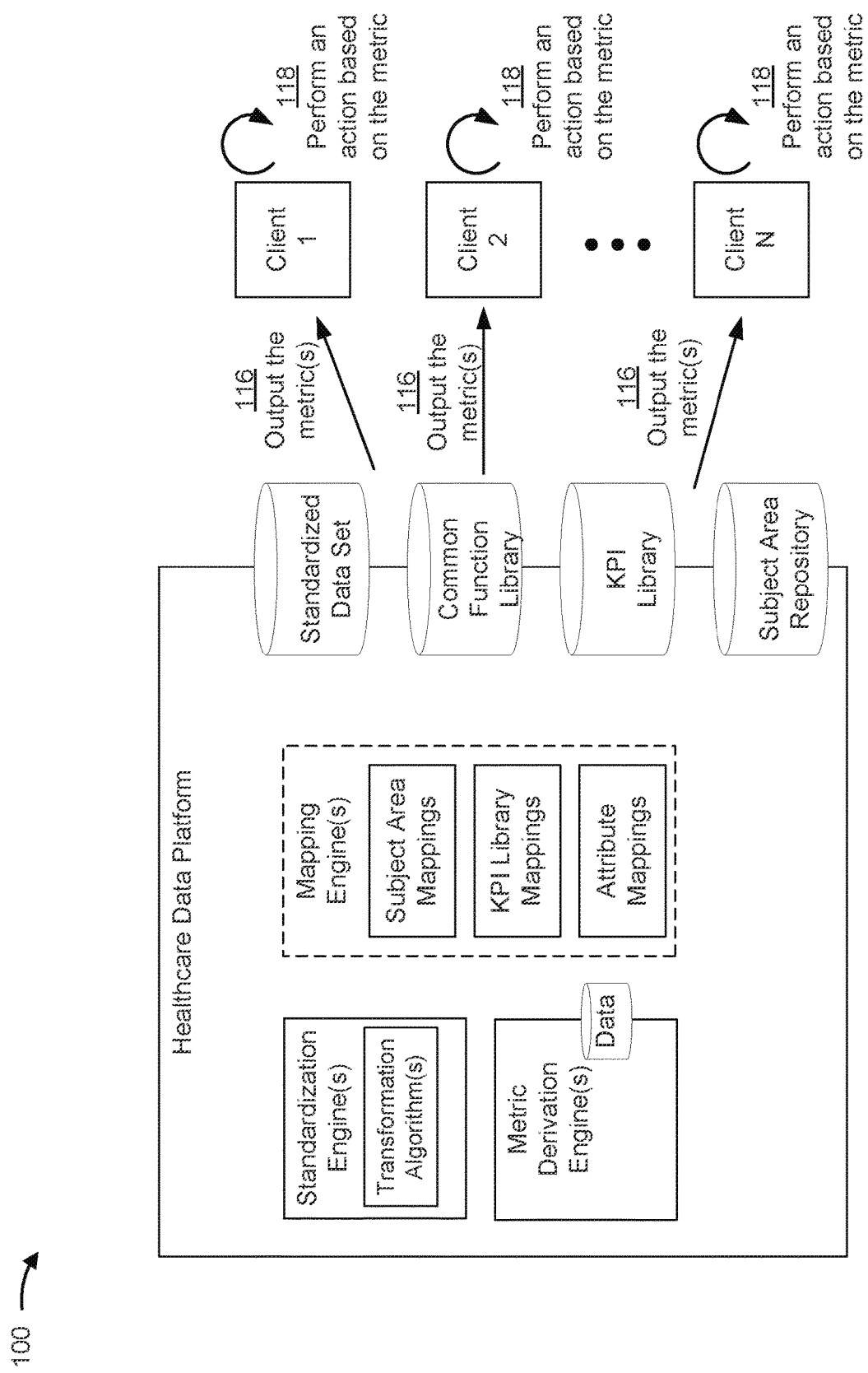

As shown in FIG. 1E, and by reference number 116, the healthcare data platform may output the generated metrics. The healthcare data platform may post the metrics to the healthcare EDI for consumption by one or more data clients (e.g., healthcare data clients), export the metrics to the one or more data clients, stream the metrics to the one or more data clients, post it to a client file system, and/or the like.

As shown by reference number 118, one or more actions may be performed based on determining the metrics. As examples of such actions, a data client may be caused to pay a claim, deny a claim, enroll an individual in an insurance policy or plan, assign a member to a healthcare provider, and/or the like, based on the metrics output by the healthcare data platform. Further, a machine (e.g., a computer, a mobile device, etc.) may be used to take a healthcare measurement, check a member into a healthcare facility or institution (e.g., using a self-check-in kiosk, a mobile device, etc.), cause a device in a healthcare facility or institution to power on or power off, cause a notification to be provided to a healthcare provider, a claims provider, and/or an individual, and/or the like. Further examples of actions that may be performed based on determining the metrics include causing a payment to be made, adding benefits or services provided to a patient, automating communications between healthcare entities, reducing waiting times in a healthcare facility or institution, scaling up computing resources for processing payments or claims by a healthcare entity, and/or the like. In this way, automated metric determination and/or output improves the efficiency and timeliness of performing actions based on the metrics.

In this way, a healthcare data platform may be provided that is flexible, scalable, and incorporates intelligent groupings or mappings to create one or more standardizing data sets based on data files having different notations and/or EDI formats. By standardizing and intelligently mapping the millions, billions, or more data files or records received from the healthcare EDI, computing resources that would otherwise be needed to decode individual data files are conserved, reduced, and/or obviated. Furthermore, the healthcare data platform may automate the generation or derivation of metrics from standardized data sets and, thus, conserve resources that would otherwise be needed to manually generate such metrics.

In this way, several different stages of the process for data extraction, transformation, and loading are automated, which may remove human subjectivity and waste from the process, and which may improve speed and efficiency of the process and conserve computing resources (e.g., processor resources, memory resources, and/or the like). Furthermore, implementations described herein use a rigorous, computerized process to perform tasks or roles that were not previously performed or were previously performed using subjective human intuition or input. For example, currently there does not exist a technique to automate data extraction, transformation, and loading for data files having different notations and/or formats. Finally, automating the process for data extraction, transformation, and loading as described herein conserves computing resources (e.g., processor resources, memory resources, and/or the like) that would otherwise be wasted in attempting to decode data files, identify attributes, and/or generate metrics.

As indicated above, FIGS. 1A-1E are provided merely as an example. Other examples are possible and may differ from what was described with regard to FIGS. 1A-1E.

Figure 2:
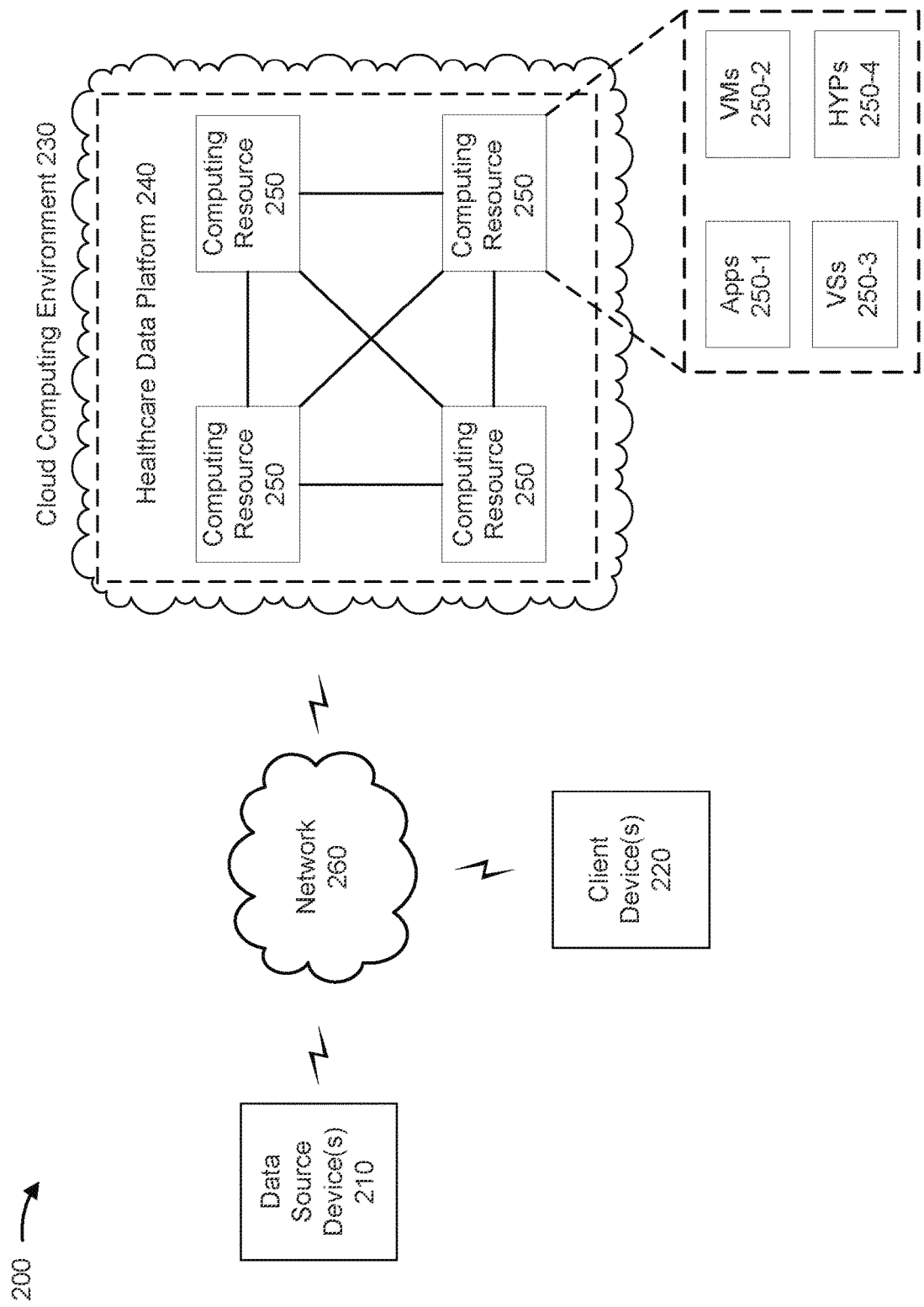
FIG. 2 is a diagram of an example environment in which systems and/or methods, described herein, may be implemented.

FIG. 2 is a diagram of an example environment 200 in which systems and/or methods, described herein, may be implemented. As shown in FIG. 2, environment 200 may include a data source device 210, a client device 220, a cloud computing environment 230, a healthcare data platform 240, a computing resource 250, and a network 260. Devices of environment 200 may interconnect via wired connections, wireless connections, or a combination of wired and wireless connections.

Data source device 210 includes one or more devices capable of sending, receiving, generating, storing, processing, communicating, and/or providing healthcare data, using a healthcare EDI, for purposes relating to an analysis of the healthcare data. For example, data source device 210 may include a server (e.g., in a data center or a cloud computing environment), a data center (e.g., a multi-server micro data center), a workstation computer, a virtual machine (VM) provided in a cloud computing environment, or a similar type of device. In some implementations, data source device 210 may provide, to healthcare data platform 240, information related to health insurance transactions, claims, eligibility, enrollment, providers, medical records, and/or the like for analysis as described elsewhere herein. Additionally, or alternatively, data source device 210 may store information related to health insurance transactions, claims, eligibility, enrollment, providers, medical records and/or the like, as described elsewhere herein.

Client device 220 includes one or more devices capable of sending, receiving, generating, storing, processing, communicating, consuming, and/or providing healthcare data, using a healthcare EDI, for purposes relating to an analysis of the healthcare data. For example, client device 220 may include a server, a computer (e.g., a desktop computer, a laptop computer, a tablet computer, etc.), a mobile phone (e.g., a smart phone or a radiotelephone), a wearable communication device (e.g., a smart wristwatch or a pair of smart eyeglasses), or a similar type of device. In some implementations, client device 220 may receive data associated with an analysis of the healthcare data that healthcare data platform 240 has performed, as described elsewhere herein. Additionally, or alternatively, client device 220 may provide information for display (e.g., information related to an analysis of healthcare data) and/or utilize the data to perform additional analyses, pay health insurance claims, deny health insurance claims, enroll members, assign providers, and/or the like, as described elsewhere herein.

Cloud computing environment 230 includes an environment that delivers computing as a service, whereby shared resources, services, etc. may be provided to healthcare data platform 240. Cloud computing environment 230 may provide computation, software, data access, storage, and/or other services that do not require end-user knowledge of a physical location and configuration of a system and/or a device that delivers the services. As shown, cloud computing environment 230 may include a healthcare data platform 240 and a computing resource 250.

Healthcare data platform 240 includes one or more devices capable of analyzing data received or obtained from a healthcare EDI. For example, healthcare data platform 240 may include a cloud server or a group of cloud servers. In some implementations, healthcare data platform 240 may be designed to be modular such that certain software components can be swapped in or out depending on a particular need. As such, healthcare data platform 240 may be easily and/or quickly reconfigured for different uses.

In some implementations, as shown, healthcare data platform 240 may be hosted in cloud computing environment 230. Notably, while implementations described herein describe healthcare data platform 240 as being hosted in cloud computing environment 230, in some implementations, healthcare data platform 240 may not be cloud-based (i.e., may be implemented outside of a cloud computing environment) or may be partially cloud-based.

Computing resource 250 includes one or more personal computers, workstation computers, server devices, or other types of computation and/or communication devices. In some implementations, computing resource 250 may host healthcare data platform 240. The cloud resources may include compute instances executing in computing resource 250, storage devices provided in computing resource 250, data transfer devices provided by computing resource 250, etc. In some implementations, computing resource 250 may communicate with other computing resources 250 via wired connections, wireless connections, or a combination of wired and wireless connections.

As further shown in FIG. 2, computing resource 250 may include a group of cloud resources, such as one or more applications ("APPs") 250-1, one or more virtual machines ("VMs") 250-2, virtualized storage ("VSs") 250-3, one or more hypervisors ("HYPs") 250-4, or the like.

Application 250-1 includes one or more software applications that may be provided to or accessed by client device 220. Application 250-1 may eliminate a need to install and execute the software applications on client device 220. For example, application 250-1 may include software associated with healthcare data platform 240 and/or any other software capable of being provided via cloud computing environment 230. In some implementations, one application 250-1 may send/receive information to/from one or more other applications 250-1, via virtual machine 250-2.

Virtual machine 250-2 includes a software implementation of a machine (e.g., a computer) that executes programs like a physical machine. Virtual machine 250-2 may be either a system virtual machine or a process virtual machine, depending upon use and degree of correspondence to any real machine by virtual machine 250-2. A system virtual machine may provide a complete system platform that supports execution of a complete operating system ("OS"). A process virtual machine may execute a single program, and may support a single process. In some implementations, virtual machine 250-2 may execute on behalf of a user (e.g., client device 220), and may manage infrastructure of cloud computing environment 230, such as data management, synchronization, or long-duration data transfers.

Virtualized storage 250-3 includes one or more storage systems and/or one or more devices that use virtualization techniques within the storage systems or devices of computing resource 250. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 250-4 provides hardware virtualization techniques that allow multiple operating systems (e.g., "guest operating systems") to execute concurrently on a host computer, such as computing resource 250. Hypervisor 250-4 may present a virtual operating platform to the guest operating systems, and may manage the execution of the guest operating systems. Multiple instances of a variety of operating systems may share virtualized hardware resources.

Network 260 includes one or more wired and/or wireless networks. For example, network 260 may include a cellular network (e.g., a long-term evolution (LTE) network, a code division multiple access (CDMA) network, a 3G network, a 4G network, a 5G network, another type of next generation network, etc.), a public land mobile network (PLMN), a local area network (LAN), a wide area network (WAN), a metropolitan area network (MAN), a telephone network (e.g., the Public Switched Telephone Network (PSTN)), a communications network, a private network, an ad hoc network, an intranet, the Internet, a fiber optic-based network, a cloud computing network, or the like, and/or a combination of these or other types of networks.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
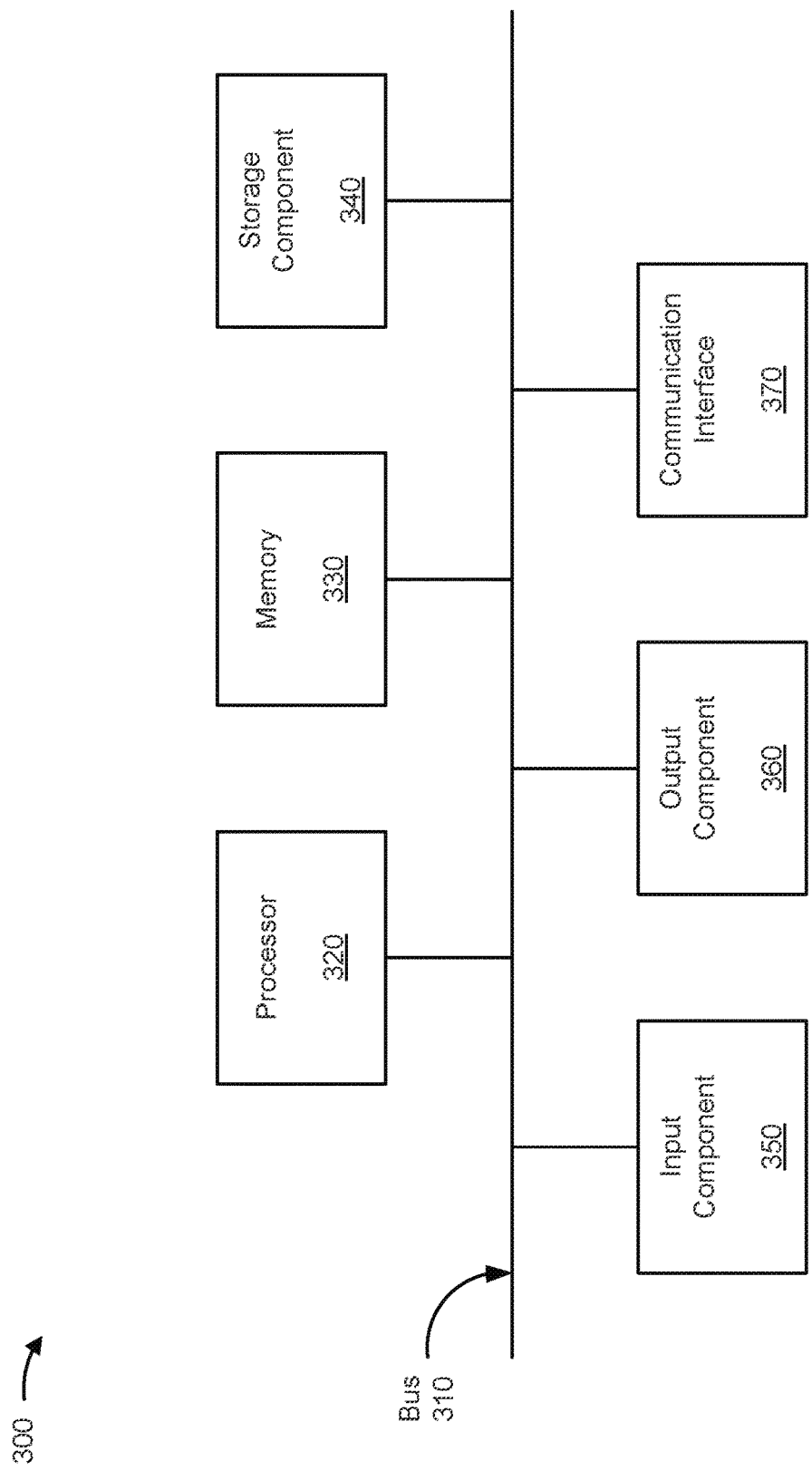
FIG. 3 is a diagram of example components of one or more devices of FIG. 2.

FIG. 3 is a diagram of example components of a device 300. Device 300 may correspond to data source device 210, client device 220, healthcare data platform 240, and/or computing resource 250. In some implementations, data source device 210, client device 220, healthcare data platform 240, and/or computing resource 250 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more light-emitting diodes (LEDs)).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, or the like.

Device 300 may perform one or more processes described herein. Device 300 may perform these processes based on to processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
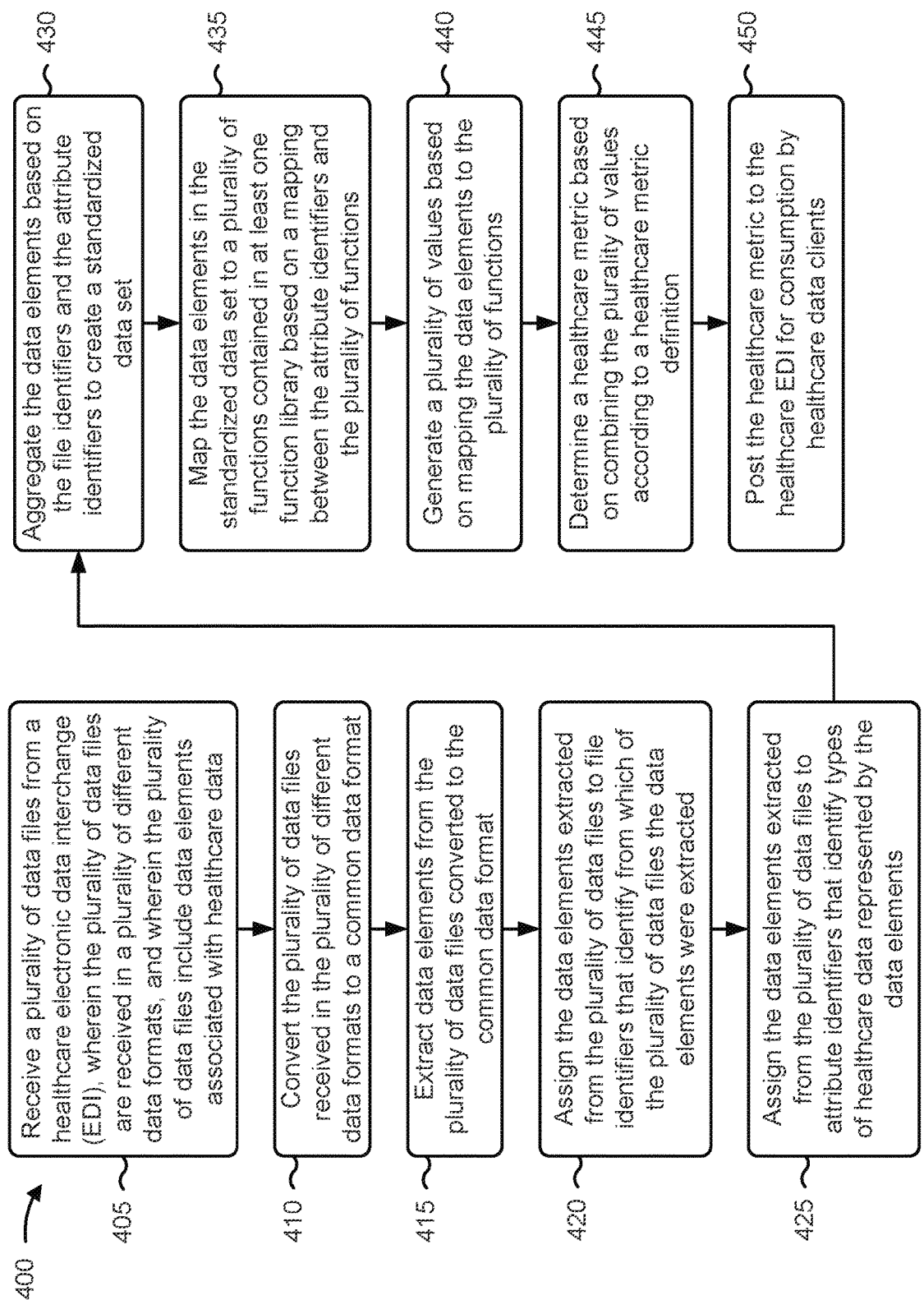
FIG. 4 is a flow chart of an example process for automated data extraction, transformation, and/or loading.

FIG. 4 is a flow chart of an example process 400 for automated data extraction, transformation, and/or loading. In some implementations, one or more process blocks of FIG. 4 may be performed by a healthcare data platform (e.g., healthcare data platform 240), which may include a computing resource (e.g., computing resource 250) of a cloud computing environment. In some implementations, one or more process blocks of FIG. 4 may be performed by another device or a group of devices separate from or including healthcare data platform (e.g., healthcare data platform 240), such as a data source device (e.g., data source device(s) 210) or a client device (e.g., client device(s) 220).

As shown in FIG. 4, process 400 may include receiving a plurality of data files from a healthcare EDI, wherein the plurality of data files are received in a plurality of different data formats, and wherein the plurality of data files include data elements associated with healthcare data (block 405). For example, the healthcare data platform (e.g., using processor 320, memory 330, storage component 340, input component 350, communication interface 370, computing resource 250, and/or the like) may receive a plurality of data files from a healthcare EDI, as described above in connection with FIGS. 1A-1E. In some implementations, the plurality of data files are received in a plurality of different data formats. In some implementations, the plurality of data files include data elements associated with healthcare data.

As further shown in FIG. 4, process 400 may include converting the plurality of data files received in the plurality of different data formats to a common data format (block 410). For example, the healthcare data platform (e.g., using processor 320, memory 330, storage component 340, computing resource 250, and/or the like) may convert the plurality of data files received in the plurality of different data formats to a common data format, as described above in connection with FIGS. 1A-1E.

As further shown in FIG. 4, process 400 may include extracting data elements from the plurality of data files converted to the common data format (block 415). For example, the healthcare data platform (e.g., using processor 320, memory 330, storage component 340, computing resource 250, and/or the like) may extract data elements from the plurality of data files convened to the common data format, as described above in connection with FIGS. 1A-1E.

As further shown in FIG. 4, process 400 may include assigning the data elements extracted from the plurality of data files to file identifiers that identify from which of the plurality of data files the data elements were extracted (block 420). For example, the healthcare data platform (e.g., using processor 320, memory 330, storage component 340, computing resource 250, and/or the like) may assign the data elements extracted from the plurality of data files to file identifiers that identify from which of the plurality of data files the data elements were extracted, as described above in connection with FIGS. 1A-1E.

As further shown in FIG. 4, process 400 may include assigning the data elements extracted from the plurality of data files to attribute identifiers that identify types of healthcare data represented by the data elements (block 425). For example, the healthcare data platform (e.g., using processor 320, memory 330, storage component 340, input component 350, communication interface 370, computing resource 250, and/or the like) may assign the data elements extracted from the plurality of data files to attribute identifiers that identify types of healthcare data represented by the data elements, as described above in connection with FIGS. 1A-1E.

As further shown in FIG. 4, process 400 may include aggregating the data elements based on the file identifiers and the attribute identifiers to create a standardized data set (block 430). For example, the healthcare data platform (e.g., using processor 320, memory 330, storage component 340, computing resource 250, and/or the like) may aggregate the data elements based on the file identifiers and the attribute identifiers to create a standardized data set, as described above in connection with FIGS. 1A-1E.

As further shown in FIG. 4, process 400 may include mapping the data elements in the standardized data set to a plurality of functions contained in at least one function library based on a mapping between the attribute identifiers and the plurality of functions (block 435). For example, the healthcare data platform (e.g., using processor 320, memory 330, storage component 340, computing resource 250, and/or the like) may map the data elements in the standardized data set to a plurality of functions contained in at least one function library based on a mapping between the attribute identifiers and the plurality of functions, as described above in confection with FIGS. 1A-1E.

As further shown in FIG. 4, process 400 may include generating a plurality of values based on mapping the data elements to the plurality of functions (block 440). For example, the healthcare data platform (e.g., using processor 320, memory 330, storage component 340, computing resource 250, and/or the like) may generate a plurality of values based on mapping the data elements to the plurality of functions, as described above in connection with FIGS. 1A-1E.

As further shown in FIG. 4, process 400 may include determining a healthcare metric based on combining the plurality of values according to a healthcare metric definition (block 445). For example, the healthcare data platform (e.g., using processor 320, memory 330, storage component 340, input component 350, communication interface 370, computing resource 250, and/or the like) may determine a healthcare metric based on combining the plurality of values according to a healthcare metric definition, as described above in connection with FIGS. 1A-1E.

As further shown in FIG. 4, process 400 may include posting the healthcare metric to the healthcare EDI for consumption by healthcare data clients (block 450). For example, the healthcare data platform (e.g., using processor 320, memory 330, storage component 340, output component 360, communication interface 370, computing resource 250, and/or the like) may post the healthcare metric to the healthcare EDI for consumption by healthcare data clients, as described above in connection with FIGS. 1A-1E.

Process 400 may include additional implementations, such as any single implementation or any combination of implementations described below and/or in connection with one or more other processes described elsewhere herein.

In some implementations, the healthcare data platform may extract a first data element from a first data file of the plurality of data files, extract a second data element from a second data file of the plurality of data files, determine that the first data element, from the first data file, requires a data transformation based on extracting the first data element from the first data file, and determine that the second data element, from the second data file, requires the data transformation based on extracting the second data element from the second data file. The healthcare data platform may map the first data element to a common transformation algorithm, map the second data element to the common transformation algorithm, transform the first data element, using the common transformation algorithm, into a modified first data element, and transform the second data element, using the common transformation algorithm, into a modified second data element. The healthcare data platform may assign the modified first data element to a first attribute identifier, and assign the modified second data element to the first attribute identifier.

In some implementations, when assigning the data elements extracted from the plurality of data files to the attribute identifiers, the healthcare data platform may examine a data file, of the plurality of data files, to identify a combination of data elements present in the data file, and may determine, using a machine learning model, a score for a data element in the data file based on the combination of data elements present in the data file, and may assign the data element to one of the attribute identifiers based on the score, in some implementations, the score may predict a type of healthcare data represented by the data element based on the combination of data elements present in the data file.

In some implementations, the healthcare data platform may examine a data file, of the plurality of data files, to identify a combination of data elements present in the data file, may determine, using a machine learning model, a score for the data file based on the combination of data elements present in the data file, and may assign the data file to a healthcare subject area repository based on the score. In some implementations, the score may predict a healthcare subject area associated with the data file based on the combination of data elements present in the data file.

In some implementations, the healthcare data platform may examine the standardized data set to identify the attribute identifiers present in the standardized data set, may determine, using a data model, a list of healthcare metrics that are derivable from the standardized data set based on the attribute identifiers present in the standardized data set, and may present the list of healthcare metrics that are derivable from the standardized data set to one or more healthcare data clients.

In some implementations, the healthcare data platform may validate decimal and integer fields in the plurality of data files converted to the common data format. In some implementations, the healthcare data platform may calculate a plurality of KPIs based on mapping the data elements in the standardized data set to the plurality of functions contained in the at least one function library, and may post the plurality of KPIs to the healthcare EDI for consumption by healthcare data clients. In some implementations, the plurality of data files may be received in two or more data formats, which may include a HL7 message format, a DICOM message format, a XML message format, a JSON message format, and/or a NCPDP message format.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Figure 5:
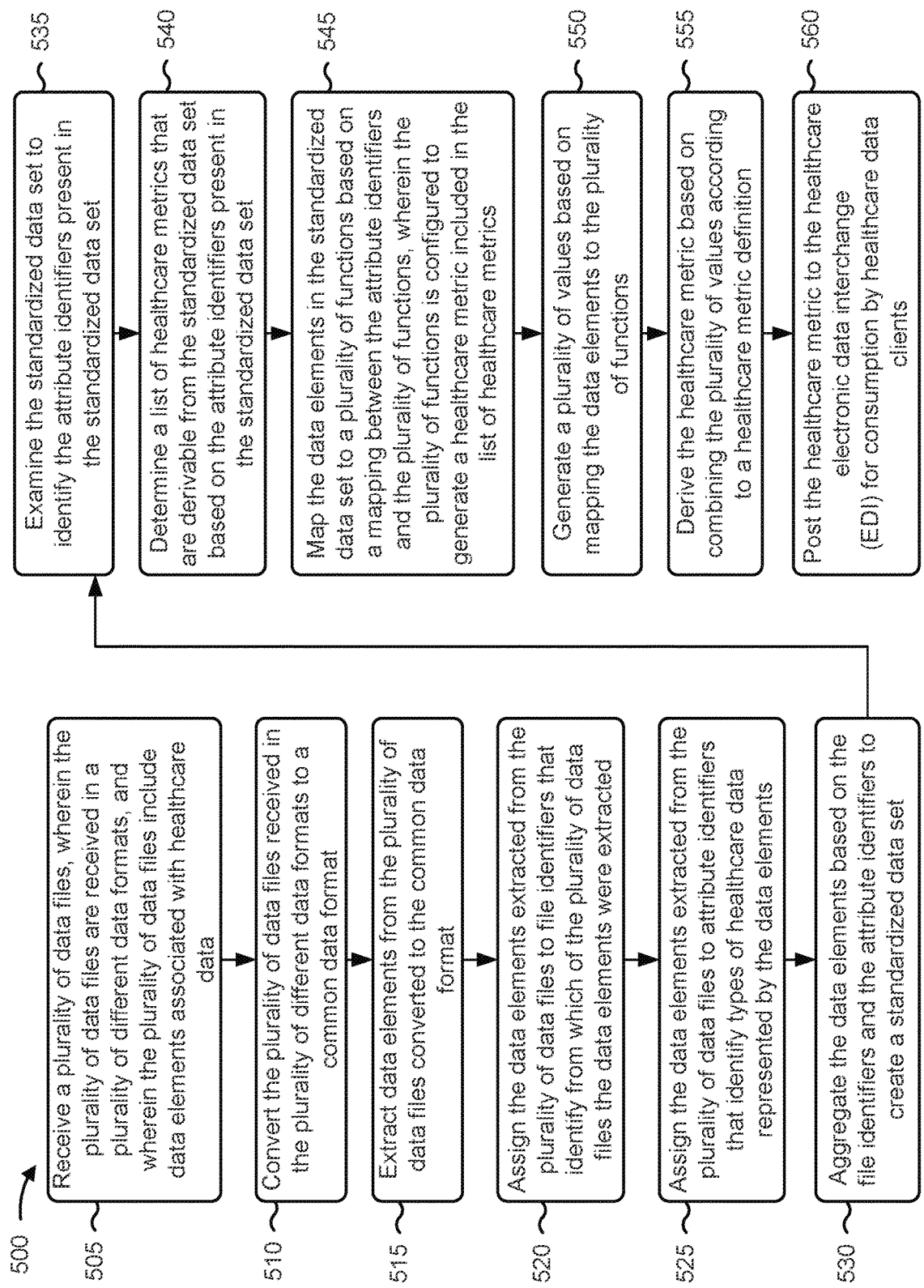
FIG. 5 is a flow chart of an example process for automated data extraction, transformation, and/or loading.

FIG. 5 is a flow chart of an example process 500 for automated data extraction, transformation, and/or loading. In some implementations, one or more process blocks of FIG. 5 may be performed by a healthcare data platform (e.g., healthcare data platform 240), which may include a computing resource (e.g., computing resource 250) of a cloud environment. In some implementations, one or more process blocks of FIG. 5 may be performed by another device or a group of devices separate from or including healthcare data platform (e.g., healthcare data platform 240), such as a data source (e.g., data source device(s) 210) or a client device (e.g., client device(s) 220).

As shown in FIG. 5, process 500 may include receiving a plurality of data files, wherein the plurality of data files are received in a plurality of different data formats, and wherein the plurality of data files include data elements associated with healthcare data (block 505). For example, the healthcare data platform (e.g., using processor 320, memory 330, storage component 340, input component 350, communication interface 370, computing resource 250, and/or the like) may receive a plurality of data files, as described above in connection with FIGS. 1A-1E. In some implementations, the plurality of data files are received in a plurality of different data formats, and the plurality of data files include data elements associated with healthcare data.

As further shown in FIG. 5, process 500 may include converting the plurality of data files received in the plurality of different data formats to a common data format (block 510). For example, the healthcare data platform (e.g., using processor 320, memory 330, storage component 340, computing resource 250, and/or the like) may convert the plurality of data files received in the plurality of different data formats to a common data format, as described above in connection with FIGS. 1A-1E.

As further shown in FIG. 5, process 500 may include extracting data elements from the plurality of data files converted to the common data format (block 515). For example, the healthcare data platform (e.g., using processor 320, memory 330, storage component 340, computing resource 250, and/or the like) may extract data elements from the plurality of data files converted to the common data format, as described above in connection with FIGS. 1A-1E.

As further shown in FIG. 5, process 500 may include assigning the data elements extracted from the plurality of data files to file identifiers that identify from which of the plurality of data files the data elements were extracted (block 520). For example, the healthcare data platform (e.g., using processor 320, memory 330, storage component 340, computing resource 250, and/or the like) may assign the data elements extracted from the plurality of data files to file identifiers that identify from which of the plurality of data files the data elements were extracted, as described above in connection with FIGS. 1A-1E.

As further shown in FIG. 5, process 500 may include assigning the data elements extracted from the plurality of data files to attribute identifiers that identify types of healthcare data represented by the data elements (block 525). For example, the healthcare data platform (e.g., using processor 320, memory 330, storage component 340, computing resource 250, and/or the like) may assign the data elements extracted from the plurality of data files to attribute identifiers that identify types of healthcare data represented by the data elements, as described above in connection with FIGS. 1A-1E.

As further shown in FIG. 5, process 500 may include aggregating the data elements based on the file identifiers and the attribute identifiers to create a standardized data set (block 530). For example, the healthcare data platform (e.g., using processor 320, memory 330, storage component 340, computing resource 250, and/or the like) may aggregate the data elements based on the file identifiers and the attribute identifiers to create a standardized data set, as described above in connection with FIGS. 1A-1E.

As further shown in FIG. 5, process 500 may include examining the standardized data set to identify the attribute identifiers present in the standardized data set (block 535). For example, the healthcare data platform (e.g., using processor 320, memory 330, storage component 340, computing resource 250, and/or the like) may examine the standardized data set to identify the attribute identifiers present in the standardized data set, as described above in connection with FIGS. 1A-1E.

As further shown in FIG. 5, process 500 may include determining a list of healthcare metrics that are derivable from the standardized data set based on the attribute identifiers present in the standardized data set (block 540). For example, the healthcare data platform (e.g., using processor 320, memory 330, storage component 340, computing resource 250, and/or the like) may determine, using a data model, a list of healthcare metrics that are derivable from the standardized data set based on the attribute identifiers present in the standardized data set, as described above in connection with FIGS. 1A-1E.

As further shown in FIG. 5, process 500 may include mapping the data elements in the standardized data set to a plurality of functions contained in at least one function library based on a mapping between the attribute identifiers and the plurality of functions, wherein the plurality of functions is configured to generate a healthcare metric included in the list of healthcare metrics (block 545). For example, the healthcare data platform (e.g., using processor 320, memory 330, storage component 340, computing resource 250, and/or the like) may map the data elements in the standardized data set to a plurality of functions based on a mapping between the attribute identifiers and the plurality of functions, as described above in connection with FIGS. 1A-1E. In some implementations, the plurality of functions is configured to generate a healthcare metric included in the list of healthcare metrics.

As further shown in FIG. 5, process 500 may include generating a plurality of values based on mapping the data elements to the plurality of functions (block 550). For example, the healthcare data platform (e.g., using processor 320, memory 330, storage component 340, computing resource 250, and/or the like) may generate a plurality of values based on processing the data elements using the plurality of functions, as described above in connection with FIGS. 1A-1E.

As further shown in FIG. 5, process 500 may include deriving a healthcare metric based on combining the plurality of values according to a healthcare metric definition (block 555). For example, the healthcare data platform (e.g., using processor 320, memory 330, storage component 340, computing resource 250, and/or the like) may derive a healthcare metric based on combining the plurality of values according to a healthcare metric definition, as described above in connection with FIGS. 1A-1E.

As further shown in FIG. 5, process 500 may include posting the healthcare metric to the healthcare EDI for consumption by healthcare data clients (block 560). For example, the healthcare data platform (e.g., using processor 320, memory 330, storage component 340, output component 360, computing resource 250, communication interface 370, and/or the like) may post the healthcare metric to a healthcare electronic data interchange EDI for consumption by healthcare data clients, as described above in connection with FIGS. 1A-1E.

Process 500 may include additional implementations, such as any single implementation or any combination of implementations described below and/or in connection with one or more other processes described elsewhere herein.

In some implementations, the healthcare data platform may examine a data file, of the plurality of data files, to identify a combination of data elements present in the data file, may determine, using a machine learning model, a score for the data file based on the combination of data elements present in the data file, and may assign the data file to a healthcare subject area repository based on the score. In some implementations, the score may predict a healthcare subject area associated with the data file based on the combination of data elements present in the data file.

In some implementations, the attribute identifiers may be associated with a health insurance member, a health insurance claim, a healthcare provider, a hospital, and/or a pharmacy. In some implementations, the plurality of functions may be configured to calculate a plurality of KPIs associated with a healthcare subject area. In some implementations, the healthcare subject area may include a subject area relating to a pharmacy, a subject area relating to a hospital, a subject area relating to a primary care physician, and/or a subject area relating to health insurance.

In some implementations, the plurality of data files may be received from the healthcare EDI. In some implementations, the plurality of data files may be received in two or more data formats, which may include HL7 message format, a DICOM message format, a XML message format, a JSON message format, and/or a NCPDP message format.

Although FIG. 5 shows example blocks of process 500, in some implementations, process 500 may include additional blocks, fewer blocks, different blocks, or differently arranged blocks than those depicted in FIG. 5. Additionally, or alternatively, two or more of the blocks of process 500 may be performed in parallel.

Figure 6A:
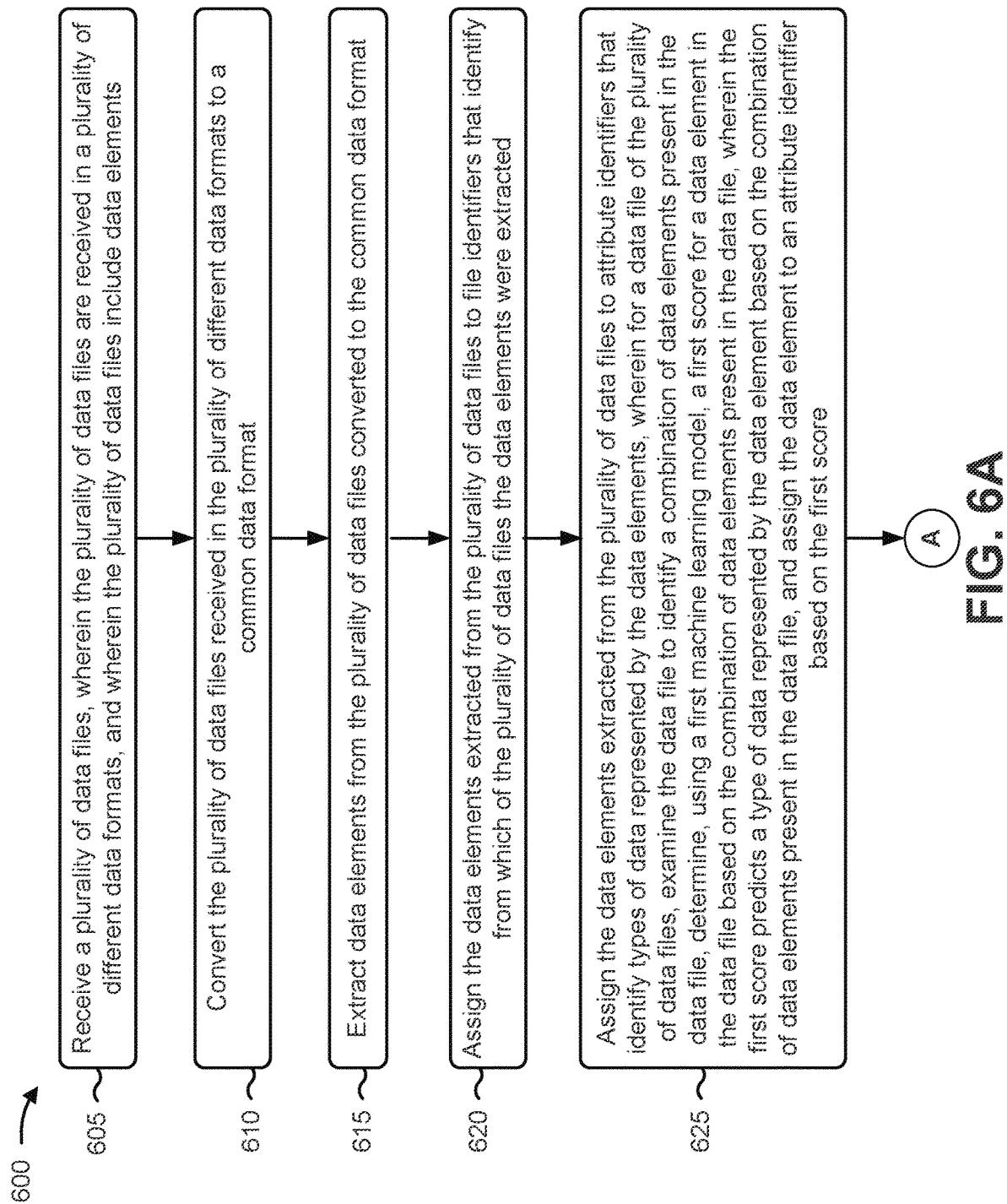
FIGS. 6A-6B are flow charts of an example process for automated data extraction, transformation, and/or loading.
Figure 6B:
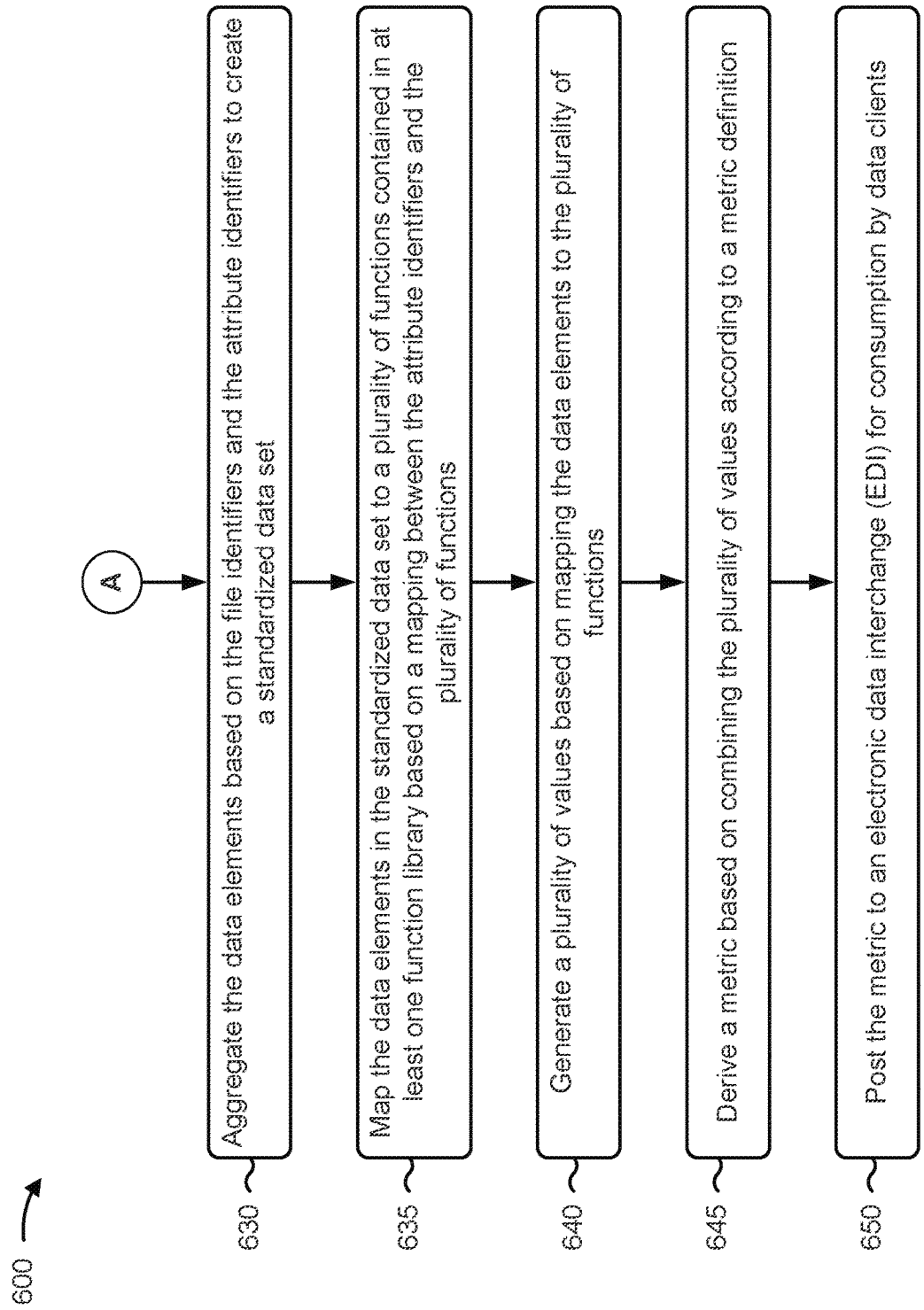

FIGS. 6A-6B are flow charts of an example process 600 for automated data extraction, transformation, and/or loading. In some implementations, one or more process blocks of FIGS. 6A-6B may be performed by a healthcare data platform (e.g., healthcare data platform 240), which may include a computing resource (e.g., computing resource 250) of a cloud computing environment. In some implementations, one or more process blocks of FIGS. 6A-6B may be performed by another device or a group of devices separate from or including healthcare data platform (e.g., healthcare data platform 240), such as a data source (e.g., data source device(s) 210) or a client device (e.g., client device(s) 220).

As shown in FIGS. 6A-6B, process 600 may include receiving a plurality of data files, wherein the plurality of data files are received in a plurality of different data formats, and wherein the plurality of data files include data elements (block 605). For example, the healthcare data platform (e.g., using processor 320, memory 330, storage component 340, input component 350, communication interface 370, computing resource 250, and/or the like) may receive a plurality of data files, as described above in connection with FIGS. 1A-1E. In some implementations, the plurality of data files are received in a plurality of different data formats. In some implementations, the plurality of data files include data elements.

As further shown in FIGS. 6A-6B, process 600 may include converting the plurality of data files received in the plurality of different data formats to a common data format (block 610). For example, the healthcare data platform (e.g., using processor 320, memory 330, storage component 340, computing resource 250, and/or the like) may convert the plurality of data files received in the plurality of different data formats to a common data format, as described above in connection with FIGS. 1A-1E.

As further shown in FIGS. 6A-6B, process 600 may include extracting data elements from the plurality of data files converted to the common data format (block 615). For example, the healthcare data platform (e.g., using processor 320, memory 330, storage component 340, computing resource 250, and/or the like) may extract data elements from the plurality of data files converted to the common data format, as described above in connection with FIGS. 1A-1E.

As further shown in FIGS. 6A-6B, process 600 may include assigning the data elements extracted from the plurality of data files to file identifiers that identify from which of the plurality of data files the data elements were extracted (block 620). For example, the healthcare data platform (e.g., using processor 320, memory 330, storage component 340, computing resource 250, and/or the like) may assign the data elements extracted from the plurality of data files to file identifiers that identify from which of the plurality of data files the data elements were extracted, as described above in connection with FIGS. 1A-1E.

As further shown in FIGS. 6A-6B, process 600 may include assigning the data elements extracted from the plurality of data files to attribute identifiers that identify types of data represented by the data elements, wherein for a data file of the plurality of data files, examine the data file to identify a combination of data elements present in the data file, determine, using a first machine learning model, a first score for a data element in the data file based on the combination of data elements present in the data file, wherein the first score predicts a type of data represented by the data element based on the combination of data elements present in the data file, and assign the data element to an attribute identifier based on the first score (block 625). For example, the healthcare data platform (e.g., using processor 320, memory 330, storage component 340, computing resource 250, and/or the like) may assign the data elements extracted from the plurality of data files to attribute identifiers that identify types of data represented by the data elements, as described above in connection with FIGS. 1A-1E. In some implementations, for a data file of the plurality of data files, the healthcare data platform may examine the data file to identify a combination of data elements present in the data file, determine, using a first machine learning model, a first score for a data element in the data file based on the combination of data elements present in the data file, wherein the first score predicts a type of data represented by the data element based on the combination of data elements present in the data file, and assign the data element to an attribute identifier based on the first score.

As further shown in FIGS. 6A-6B, process 600 may include aggregating the data elements based on the file identifiers and the attribute identifiers to create a standardized data set (block 630). For example, the healthcare data platform (e.g., using processor 320, memory 330, storage component 340, computing resource 250, and/or the like) may aggregate the data elements based on the file identifier and the attribute identifiers to create a standardized data set, as described above in connection with FIGS. 1A-1E.

As further shown in FIGS. 6A-6B process 600 may include mapping the data elements in the standardized data set to a plurality of functions contained in at least one function library based on a mapping between the attribute identifiers and the plurality of functions (block 635). For example, the healthcare data platform (e.g., using processor 320, memory 330, storage component 340, computing resource 250, and/or the like) may map the data elements in the standardized data set to a plurality of functions contained in at least one function library based on a mapping between the attribute identifiers and the plurality of functions, as described above in connection with FIGS. 1A-1E.

As further shown in FIGS. 6A-6B, process 600 may include generating a plurality of values based on mapping the data elements to the plurality of functions (block 640). For example, the healthcare data platform (e.g., using processor 320, memory 330, storage component 340, computing resource 250, and/or the like) may generate a plurality of values based on mapping the data elements to the plurality of functions, as described above in connection with FIGS. 1A-1E.

As further shown in FIGS. 6A-6B, process 600 may include deriving a metric based on combining the plurality of values according to a metric definition (block 645). For example, the healthcare data platform (e.g., using processor 320, memory 330, storage component 340, computing resource 250, and/or the like) may derive a metric based on combining the plurality of values according to a metric definition, as described above in connection with FIGS. 1A-1E.

As further shown in FIGS. 6A-6B, process 600 may include posting the metric to an EDI for consumption by data clients (block 650). For example, the healthcare data platform (e.g., using processor 320, memory 330, storage component 340, output component 360, communication interface 370, computing resource 250, and/or the like) may post the metric to an EDI for consumption by data clients, as described above in connection with FIGS. 1A-1E.

Process 600 may include additional implementations, such as any single implementation or any combination of implementations described below and/or in connection with one or more other processes described elsewhere herein.

In some implementations, the healthcare data platform may determine, using a second machine learning model, a second score for the data file based on the combination of data elements present in the data file, and may assign the data file to a subject area repository based on the second score. In some implementations, the second score may predict a subject area associated with the data file based on the combination of data elements present in the data file.

In some implementations, the healthcare data platform may examine the standardized data set to identify the attribute identifiers present in the standardized data set, may determine, using a data model, a list of metrics that are derivable from the standardized data set based on the attribute identifiers present in the standardized data set, and may present the list of metrics that are derivable from the standardized data set to one or more data clients.

In some implementations, the healthcare data platform may generate a plurality of KPIs based on mapping the data elements in the standardized data set to the plurality of functions contained in the at least one function library, and may post the plurality of KPIs to a healthcare EDI for consumption by healthcare data clients. In some implementations, the healthcare data platform may transmit the metric to one or more data clients.

Although FIGS. 6A-6B show example blocks of process 600, in some implementations, process 600 may include additional blocks, fewer blocks, different blocks, or differently arranged blocks than those depicted in FIGS. 6A-6B. Additionally, or alternatively, two or more of the blocks of process 600 may be performed in parallel.

In this way, a healthcare data platform 240 automates the transformation of raw data into structured, standardized data sets that are more consumable, and may conserve resources that would otherwise be needed to create and store individualized data sets. Healthcare data platform 240 utilizes data models and/or machine data models to recognize patterns in the data files being received from the healthcare EDI to intelligently map the data elements in the data files to common, reusable functions and automatically derive business metrics. By standardizing and intelligently mapping the millions, billions, or more data files received from the healthcare EDI, computing resources that would otherwise be needed to decode individual data files are conserved, reduced, and/or obviated. Furthermore, healthcare data platform 240 may automate the generation or derivation of metrics from standardized data sets and, thus, conserve resources that would otherwise be needed to manually generate such metrics. By virtue of re-using common data transformations and/or functions, healthcare data platform 240 conserves resources that would otherwise be needed to duplicate such functions across multiple different EDI formats.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, and/or a combination of hardware and software.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, or the like.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware can be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Additionally, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Additionally, as used herein, the terms "has," "have," "having," or the like are intended to be open-ended terms. Further, the phrase "based on" is intended to refer to "based, at least in part, on" unless explicitly stated otherwise.

What is claimed is:

1. A method, comprising:
   receiving, by a computing resource of a cloud computing environment, a plurality of data files from a healthcare electronic data interchange (EDI),
      wherein the plurality of data files are received in a plurality of different data formats, and
      wherein the plurality of data files include data elements associated with healthcare data;
   converting, by the computing resource of the cloud computing environment, the plurality of data files received in the plurality of different data formats to a common data format;
   extracting, by the computing resource of the cloud computing environment, data elements from the plurality of data files converted to the common data format;
   extracting, by the computing resource of the cloud computing environment, a first data element, of the data elements, from a first data file of the plurality of data files;
   extracting, by the computing resource of the cloud computing environment, a second data element, of the data elements from a second data file of the plurality of data files;
   determining, by the computing resource of the cloud computing environment, that the first data element and the second data element require a data transformation;
   mapping, by the computing resource of the cloud computing environment, the first data element and the second data element to a common transformation algorithm;
   transforming, by the computing resource of the cloud computing environment, the first data element, using the common transformation algorithm, into a modified first data element;
   transforming, by the computing resource of the cloud computing environment, the second data element, using the common transformation algorithm, into a modified second data element;
   assigning, by the computing resource of the cloud computing environment, the data elements extracted from the plurality of data files to file identifiers that identify from which of the plurality of data files the data elements were extracted;
   assigning, by the computing resource of the cloud computing environment, the data elements extracted from the plurality of data files to attribute identifiers that identify types of healthcare data represented by the data elements;
   assigning, by the computing resource of the cloud computing environment, the modified first data element and the modified second data element to a first attribute identifier of the attribute identifiers;
   aggregating, by the computing resource of the cloud computing environment, the data elements based on the file identifiers and the attribute identifiers to create a standardized data set;
   mapping, by the computing resource of the cloud computing environment, the data elements in the standardized data set to a plurality of functions contained in at least one function library based on a mapping between the attribute identifiers and the plurality of functions;
   generating, by the computing resource of the cloud computing environment, a plurality of values based on mapping the data elements to the plurality of functions;
   determining, by the computing resource of the cloud computing environment, a healthcare metric based on combining the plurality of values according to a healthcare metric definition; and
   posting, by the computing resource of the cloud computing environment, the healthcare metric to the healthcare EDI for consumption by healthcare data clients.

2. The method of claim 1, wherein assigning the data elements extracted from the plurality of data files to the attribute identifiers comprises:
   examining a data file, of the plurality of data files, to identify a combination of data elements present in the data file; and
   determining, using a machine learning model, a score for a data element in the data file based on the combination of data elements present in the data file,
      wherein the score predicts a type of healthcare data represented by the data element based on the combination of data elements present in the data file; and
   assigning the data element to one of the attribute identifiers based on the score.

3. The method of claim 1, further comprising:
   examining a data file, of the plurality of data files, to identify a combination of data elements present in the data file; and
   determining, using a machine learning model, a score for the data file based on the combination of data elements present in the data file, wherein the score predicts a healthcare subject area associated with the data file based on the combination of data elements present in the data file; and assigning the data file to a healthcare subject area repository based on the score.

4. The method of claim 1, further comprising:

examining the standardized data set to identify the attribute identifiers present in the standardized data set;

determining, using a data model, a list of healthcare metrics that are derivable from the standardized data set based on the attribute identifiers present in the standardized data set; and presenting the list of healthcare metrics that are derivable from the standardized data set to one or more healthcare data clients.

5. The method of claim 1, further comprising validating decimal and integer fields in the plurality of data files converted to the common data format.

6. The method of claim 1, further comprising:

calculating a plurality of key performance indicators (KPIs) based on mapping the data elements in the standardized data set to the plurality of functions contained in the at least one function library; and posting the plurality of KPIs to the healthcare EDI for consumption by healthcare data clients.

7. The method of claim 1, wherein the plurality of data files are received in two or more data formats including:

a HL7 message format, a DICOM message format, a XML, message format, a JSON message format, or a NCPDP message format.

8. A device, comprising:

one or more memory devices; and one or more processors, implemented at least partially in hardware and communicatively coupled to the one or more memory devices, to:

receive a plurality of data files, wherein the plurality of data files are received in a plurality of different data formats, and wherein the plurality of data files include data elements associated with healthcare data;

convert the plurality of data files received in the plurality of different data formats to a common data format;

extract data elements from the plurality of data files converted to the common data format;

extract a first data element, of the data elements, from a first data file of the plurality of data files;

extract a second data element, of the data elements from a second data file of the plurality of data files;

determine that the first data element and the second data element require a data transformation;

map the first data element and the second data element to a common transformation algorithm;

transform the first data element, using the common transformation algorithm, into a modified first data element;

transform the second data element, using the common transformation algorithm, into a modified second data element;

assign the data elements extracted from the plurality of data files to file identifiers that identify from which of the plurality of data files the data elements were extracted;

assign the data elements extracted from the plurality of data files to attribute identifiers that identify types of healthcare data represented by the data elements;

assign the modified first data element and the modified second data element to a first attribute identifier of the attribute identifiers;

aggregate the data elements based on the file identifiers and the attribute identifiers to create a standardized data set;

examine the standardized data set to identify the attribute identifiers present in the standardized data set;

determine, using a data model, a list of healthcare metrics that are derivable from the standardized data set based on the attribute identifiers present in the standardized data set;

map the data elements in the standardized data set to a plurality of functions based on a mapping between the attribute identifiers and the plurality of functions, wherein the plurality of functions is configured to generate a healthcare metric included in the list of healthcare metrics;

generate a plurality of values based on processing the data elements using the plurality of functions;

derive the healthcare metric based on combining the plurality of values according to a healthcare metric definition; and post the healthcare metric to a healthcare electronic data interchange (EDI) for consumption by healthcare data clients.

9. The device of claim 8, wherein the one or more processors are further configured to:

examine a data file, of the plurality of data files, to identify a combination of data elements present in the data file;

determine, using a machine learning model, a score for the data file based on the combination of data elements present in the data file, wherein the score predicts a healthcare subject area associated with the data file based on the combination of data elements present in the data file; and assign the data file to a healthcare subject area repository based on the score.

10. The device of claim 8, wherein the attribute identifiers are associated with a health insurance member, a health insurance claim, a healthcare provider, a hospital, or a pharmacy.

11. The device of claim 8, wherein the plurality of functions is configured to calculate a plurality of key performance indicators (KPIs) associated with a healthcare subject area.

12. The device of claim 11, wherein the healthcare subject area includes one of:

a first subject area relating to a pharmacy, a second subject area relating to a hospital, a third subject area relating to a primary care physician, or a fourth subject area relating to health insurance.

13. The device of claim 8, wherein the plurality of data files are received from the healthcare EDI.

14. The device of claim 13, wherein the plurality of data files are received in two or more data formats including:

a HL7 message format, a DICOM message format, a XML message format, a JSON message format, or a NCPDP message format.

15. A non-transitory computer-readable medium storing instructions, the instructions comprising:

one or more instructions that, when executed by one or more processors, cause the one or more processors of a device to:
receive a plurality of data files,
wherein the plurality of data files are received in a plurality of different data formats, and
wherein the plurality of data files include data elements;
convert the plurality of data files received in the plurality of different data formats to a common data format;
extract data elements from the plurality of data files converted to the common data format;
extract a first data element, of the data elements, from a first data file of the plurality of data files;
extract a second data element, of the data elements from a second data file of the plurality of data files;
determine that the first data element and the second data file require a data transformation;
map the first data element and the second data element to a common transformation algorithm;
transform the first data element, using the common transformation algorithm, into a modified first data element;
transform the second data element, using the common transformation algorithm, into a modified second data element;
assign the data elements extracted from the plurality of data files to file identifiers that identify from which of the plurality of data files the data elements were extracted;
assign the data elements extracted from the plurality of data files to attribute identifiers that identify types of data represented by the data elements,
wherein for a data file of the plurality of data files:
examine the data file to identify a combination of data elements present in the data file,
determine, using a first machine learning model, a first score for a data element in the data file based on the combination of data elements present in the data file,
wherein the first score predicts a type of data represented by the data element based on the combination of data elements present in the data file, and
assign the data element to an attribute identifier based on the first score;
assign the modified first data element and the modified second data element to a first attribute identifier of the attribute identifiers;
aggregate the data elements based on the file identifiers and the attribute identifiers to create a standardized data set;
map the data elements in the standardized data set to a plurality of functions contained in at least one function library based on a mapping between the attribute identifiers and the plurality of functions;
generate a plurality of values based on mapping the data elements to the plurality of functions;
derive a metric based on combining the plurality of values according to a metric definition; and
post the metric to an electronic data interchange (EDI) for consumption by data clients.

16. The non-transitory computer-readable medium of claim 15, wherein the one or more instructions, when executed by the one or more processors, further cause the one or more processors to:
determine, using a second machine learning model, a second score for the data file based on the combination of data elements present in the data file,
wherein the second score predicts a subject area associated with the data file based on the combination of data elements present in the data file; and
assign the data file to a subject area repository based on the second score.

17. The non-transitory computer-readable medium of claim 15, wherein the one or more instructions, when executed by the one or more processors, further cause the one or more processors to:
examine the standardized data set to identify the attribute identifiers present in the standardized data set;
determine, using a data model, a list of metrics that are derivable from the standardized data set based on the attribute identifiers present in the standardized data set; and
present the list of metrics that are derivable from the standardized data set to one or more data clients.

18. The non-transitory computer-readable medium of claim 15, wherein the one or more instructions, when executed by the one or more processors, further cause the one or more processors to:
generate a plurality of key performance indicators (KPIs) based on mapping the data elements in the standardized data set to the plurality of functions contained in the at least one function library; and
post the plurality of KPIs to the EDI for consumption by healthcare data clients.

19. The non-transitory computer-readable medium of claim 15, wherein the one or more instructions, when executed by the one or more processors, further cause the one or more processors to:
transmit the metric to one or more data clients.

20. The method of claim 1, further comprising:
receiving the plurality of data files in a streaming manner; and
receiving the plurality of data files using application programming interface (API) calls.

* * * * *